United States Patent [19]

Meuer et al.

[11] Patent Number: 5,510,461
[45] Date of Patent: Apr. 23, 1996

[54] PP: A NEWLY IDENTIFIED CD45-ASSOCIATED PROTEIN

[75] Inventors: Stefan Meuer; Burkhart Schraven, both of Heidelberg, Germany; David Schoenhaut, Worcester; Sheldon Ratnofsky, West Newton, both of Mass.

[73] Assignee: BASF Akteingesellschaft, Ludwigshafen, Germany

[21] Appl. No.: 197,793

[22] Filed: Feb. 14, 1994

Related U.S. Application Data

[63] Continuation-in-part of Ser. No. 4,199, Jan. 13, 1993, abandoned, which is a continuation of Ser. No. 688,019, Apr. 19, 1991, abandoned.

[51] Int. Cl.$^6$ .............................. C12Q 1/68; C07K 1/00; C07K 14/00; C07K 16/00
[52] U.S. Cl. ........................... 530/350; 530/387.9; 435/6
[58] Field of Search .................................. 435/6; 514/12; 530/350, 387.9

[56] References Cited

FOREIGN PATENT DOCUMENTS

WO92/02554  2/1992  WIPO.

OTHER PUBLICATIONS

Altin, J. B. et al. (1994) "Evidence for an Association of CD45 with 32000–33000 MW Phosphoprotein of Murine T and B Lymphocytes", *Immunology* vol. 83, pp. 420–429.
Brown et al. (1994) "Multiple Components of the B Cell Antigen Receptor Complex Associate with the Protein Tyrosine Kinase Phosphatase, CD45", *J. Biol. Chem.*, vol. 269, No. 25, pp. 17238–17244.
Schraven, B. et al. (1994) "LPAP, a Novel 32–kDa Phosphoprotein that Interacts with CD45 in Human Lymphocytes", *J. Biol. Chem.*, vol. 269, No. 46, pp. 29102–29111.
Schraven, B. et al. (1992) "Four CD45/P56lck–associated Phosphoproteins (pp. 29–pp. 32) Undergo Alterations in Human T Cell Activation", *Eur. J. Immunol.*, vol. 22, No. 7, pp. 1857–1863.
Schraven, B. et al., (1992) "Four CD45/56lck–associated Phosphoproteins (pp. 29–pp. 32) Undergo Alterations in Human T Cell Activation", *Chemical Abstracts*, vol. 117, No. 15, Abstract No. 149228.

Takeda et al., "Molecular Cloning of the CD45–associated 30–kDa Protein", *The Journal of Biological Chemistry*, vol. 269, No. 4, pp. 2357–2360, (Jan. 28, 1994).
Gyuris et al., "Cdi1, a Human G1 and S Phase Protein Phosphatase That Associates with Cdk2", *Cell*, vol. 75, pp. 791–803, (Nov. 19, 1993).
Tonks et al., "CD45, an Integral Membrane Protein Tyrosine Phosphatase", *The Journal of Biological Chemistry*, vol. 265, No. 18, pp. 10674–10680, (Jun. 25, 1990).
Schraven et al., "Triggering of the alternative pathway of human T cell activation involves members of the T 200 family of glycoproteins", *European Journal of Immunology*, vol. 19, pp. 397–403, (1989).
Ross et al., "The Association Between CD45 and LCK Does Not Require CD4 Or CD8 And Is Independent of T Cell Receptor Stimulation," *Biochemical and Biophysical Research Communications*, vol. 198, No. 1, pp. 88–96, (1994).
Schraven et al., "Alterations of CD2 association with T cell receptor signaling molecules in 'CD2 unresponsive' human T lymphocytes," *European Journal of Immunology*, vol. 23, pp. 119–123, (1993).
Schraven et al., "Four CD45/P56$^{lck}$–associated phosphoproteins (pp. 29–pp. 32) undergo alterations in human T cell activation" *European Journal of Immunology*, vol. 22, pp. 1857–1863, (1992).
Schraven et al., "A functional complex is formed in human T lymphocytes between the protein tyrosine phosphatase CD45, the protein tyrosine kinase p56$^{lck}$ and p. 32, a possible common substrate", *European Journal of Immunology*, vol. 21, pp. 2469–2477, (1991).
Kiener, et al. (1989), *J. Immunol. 143(1):23–28*.

*Primary Examiner*—Robert A. Wax
*Assistant Examiner*—Lisa J. Hobbs
*Attorney, Agent, or Firm*—Lahive & Cockfield; Giulio A. DeConti, Jr.

[57] ABSTRACT

This invention relates to a newly identified protein useful for treating diseases of the immune system, methods for obtaining said protein, isolated nucleic acids encoding said protein, and methods for obtaining inhibitors of said protein. The protein of this invention is characterized by an apparent molecular weight of about 32 kD, an isoelectric point of about 4.0–4.5 and coprecipitation with CD45. The protein may also be used in in vitro or in vivo assays to identify inhibitors of T cell activation.

4 Claims, 9 Drawing Sheets

A-D: NON REDUCING CONDITIONS
A'-D': REDUCING CONDITIONS

A: K562
B: HPB-ALL
C: LAZ 509
D: JURKAT (JMP1)
E: JURKAT (JMP 15)

PHOSPHAMINOACID ANALYSIS

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 953 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 64..681

( x i ) SEQUENCE DESCRIPTION: SEQ ID NO:1:

```
ACTTCTCGCT CGACACATCC AGAGCTGGAG GTGCGTGCCC GGCACGGAGG GGCCTGCGGA            60

CCA ATG GCT CTG CCC TGC ACC TTA GGG CTC GGG ATG CTG CTG GCC CTG            108
    Met Ala Leu Pro Cys Thr Leu Gly Leu Gly Met Leu Leu Ala Leu
    1               5                   10                  15

CCA GGG GCC TTG GGC TCG GGT GGC AGC GCG GAG GAC AGC GTG GGC TCC            156
Pro Gly Ala Leu Gly Ser Gly Gly Ser Ala Glu Asp Ser Val Gly Ser
20                  25                  30

AGC TCT GTC ACC GTT GTC CTG CTG CTG CTG CTC CTA CTG CTG GCC                204
Ser Ser Val Thr Val Val Leu Leu Leu Leu Leu Leu Leu Leu Ala
    35                  40                  45

ACT GGC CTA GCA CTG GCC TGG CGC CGC CTC AGC CGT GAC TCA GGG GGC            252
Thr Gly Leu Ala Leu Ala Trp Arg Arg Leu Ser Arg Asp Ser Gly Gly
50                  55                  60

TAC TAC CAC CCG GCC CGC CTA GGT GCC GCG CTG TGG GGC CGC ACG CGG            300
Tyr Tyr His Pro Ala Arg Leu Gly Ala Ala Leu Trp Gly Arg Thr Arg
    65                  70                  75

CGC CTG CTC TGG GCC AGC CCC CCA GGT CGC TGG CTG CAG GCC CGA GCT            348
Arg Leu Leu Trp Ala Ser Pro Pro Gly Arg Trp Leu Gln Ala Arg Ala
80                  85                  90                          95

GAG CTG GGG TCC ACA GAC AAT GAC CTT GAG CGA CAG GAG GAT GAG CAG            396
Glu Leu Gly Ser Thr Asp Asn Asp Leu Glu Arg Gln Glu Asp Glu Gln
100                 105                 110

GAC ACA GAC TAT GAC CAC GTC GCG GAT GGT GGC ATG CAG GCT GAC CCT            444
Asp Thr Asp Tyr Asp His Val Ala Asp Gly Gly Met Gln Ala Asp Pro
    115                 120                 125

GGG GAA GGC GAG CAG CAA TGT GGA GAG GCG TCC AGC CCA GAG CAG GTC            492
Gly Glu Gly Glu Gln Gln Cys Gly Glu Ala Ser Ser Pro Glu Gln Val
130                 135                 140

CCC GTG CGG GCT GAG GAA GCC AGA GAC AGT GAC ACG GAG GGC GAC CTG            540
Pro Val Arg Ala Glu Glu Ala Arg Asp Ser Asp Thr Glu Gly Asp Leu
    145                 150                 155

GTC CTC GGC TCC CCA GGA CCA GCG AGC GCA GGG GGC AGT GCT GAG GCC            588
Val Leu Gly Ser Pro Gly Pro Ala Ser Ala Gly Gly Ser Ala Glu Ala
160                 165                 170                 175
```

```
CTG CTG AGT GAC CTG CAC GCC TTT GCT GGC AGC GCA GCC TGG GAT GAC     636
Leu Leu Ser Asp Leu His Ala Phe Ala Gly Ser Ala Ala Trp Asp Asp
180                 185                 190

AGC GCC AGG GCA GCT GGG GGC CAG GGC CTC CAT GTC ACC GCA CTG         681
Ser Ala Arg Ala Ala Gly Gly Gln Gly Leu His Val Thr Ala Leu
    195                 200                 205

TAGAGGCCGG TCTTGGTGTC CCATCCCTGT CACAGCCGCT CACTCCCCGT GCCTCTGCTT   741

CCCAAGATGC CATGGCTGGA CTGGACCCCC AGCCACATG  ACCATGCCTC AGACTGTCAC   801

CCCTACCAGT TCCCAAGTCC ATGTGTACCC CGCTCACCAC GGGAACGGCC CCCCCCAACC   861

ACAGGCATCA GGCAACCATT TGAAATAAAA CTCCTTCAGC CTGTGAAAAA AAAAAAAAA    921

AAAAAAAAAA AAAAAAAAAA AAAAAAAAA AA                                  953
```

( 2 ) INFORMATION FOR SEQ ID NO:2:

( i ) SEQUENCE CHARACTERISTICS:
        ( A ) LENGTH: 206 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Leu Pro Cys Thr Leu Gly Leu Gly Met Leu Leu Ala Leu Pro
1               5                   10                  15

Gly Ala Leu Gly Ser Gly Gly Ser Ala Glu Asp Ser Val Gly Ser Ser
        20              25                  30

Ser Val Thr Val Val Leu Leu Leu Leu Leu Leu Leu Leu Ala Thr
35                  40                  45

Gly Leu Ala Leu Ala Trp Arg Arg Leu Ser Arg Asp Ser Gly Gly Tyr
        50              55                  60

Tyr His Pro Ala Arg Leu Gly Ala Ala Leu Trp Gly Arg Thr Arg Arg
65                  70                  75                  80

Leu Leu Trp Ala Ser Pro Pro Gly Arg Trp Leu Gln Ala Arg Ala Glu
85                  90                  95

Leu Gly Ser Thr Asp Asn Asp Leu Glu Arg Gln Glu Asp Glu Gln Asp
        100                 105                 110

Thr Asp Tyr Asp His Val Ala Asp Gly Gly Met Gln Ala Asp Pro Gly
115                 120                 125

Glu Gly Glu Gln Gln Cys Gly Glu Ala Ser Ser Pro Glu Gln Val Pro
        130                 135                 140

Val Arg Ala Glu Glu Ala Arg Asp Ser Asp Thr Glu Gly Asp Leu Val
145                 150                 155                 160

Leu Gly Ser Pro Gly Pro Ala Ser Ala Gly Gly Ser Ala Glu Ala Leu
        165                 170                 175

Leu Ser Asp Leu His Ala Phe Ala Gly Ser Ala Ala Trp Asp Asp Ser
        180                 185                 190

Ala Arg Ala Ala Gly Gly Gln Gly Leu His Val Thr Ala Leu
195                 200                 205
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide (v) FRAGMENT TYPE: N-terminal (xi) SEQUENCE DESCRIPTION: SEQ ID NO:3:

```
Ser Gly Gly Ser Ala Glu Asp Ser Val Gly
1               5                   10
```

(2) INFORMATION FOR SEQ ID NO:4:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

```
Gly Gly Tyr Tyr His Pro Ala Arg
1               5
```

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

```
Leu Leu Trp Ala Ser Pro Pro
1               5
```

(2) INFORMATION FOR SEQ ID NO:6:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:6:

```
Trp Leu Gln Ala Arg
1               5
```

(2) INFORMATION FOR SEQ ID NO:7:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:7:

```
Ala Ala Gly Gly Gln Gly Leu His Val Thr Ala Leu
1               5                   10
```

(2) INFORMATION FOR SEQ ID NO:8:

(i) SEQUENCE CHARACTERISTICS:
        (A) LENGTH: 11 amino acids ( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:8:

| Leu | Gly | Ser | Thr | Asp | Asn | Asp | Leu | Glu | Arg | Gln |
|---|---|---|---|---|---|---|---|---|---|---|
| 1 | | | | 5 | | | | | 10 | |

( 2 ) INFORMATION FOR SEQ ID NO:9:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:9:

| Glu | Asp | Glu | Gln | Asp | Thr | Asp | Tyr | Asp | His | Val |
|---|---|---|---|---|---|---|---|---|---|---|
| 1 | | | | 5 | | | | | 10 | |

( 2 ) INFORMATION FOR SEQ ID NO:10:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:10:

| Gly | Asp | Leu | Val | Leu | Gly | Ser | Pro | Gly | Pro | Ala | Ser | Ala | Gly | Gly | Ser |
|---|---|---|---|---|---|---|---|---|---|---|---|---|---|---|---|
| 1 | | | | 5 | | | | | 10 | | | | | 15 | |

Ala Glu ( 2 ) INFORMATION FOR SEQ ID NO:11:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( v ) FRAGMENT TYPE: internal ( x i ) SEQUENCE DESCRIPTION: SEQ ID NO:11:

| Ala | Leu | Leu | Ser | Asp | Leu | His | Ala | Phe | Ala | Gly | Ser | Ala | Ala | Trp | Asp |
|---|---|---|---|---|---|---|---|---|---|---|---|---|---|---|---|
| 1 | | | | 5 | | | | | 10 | | | | | 15 | |

| Asp | Ser | Ala | Arg | Ala |
|---|---|---|---|---|
| 20 | | | | |

( 2 ) INFORMATION FOR SEQ ID NO:12:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: primer ( x i ) SEQUENCE DESCRIPTION: SEQ ID NO:12:

YTNTCNGAYC TNCAYGC 17

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:13:

YTNTCNGAYT TRCAYGC 17

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:14:

YTNAGYGAYC TNCAYGC 17

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:15:

YTNAGYGAYT TRCAYGC 17

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:16:

GCNCKNGCNG ARTCRTC 17

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: primer (xi) SEQUENCE DESCRIPTION: SEQ ID NO:17:

GCNCKNGCRC TRTCRTC 17

(2) INFORMATION FOR SEQ ID NO:18:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: primer ( x i ) SEQUENCE DESCRIPTION: SEQ ID NO:18:

GARCARGAYA CNGAYTA                                                                17

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:19:

TCCCAGGCAG CAGAGCCAGC A                                                           21

( 2 ) INFORMATION FOR SEQ ID NO:20:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:20:

GACTAGTCGA C                                                                      11

PP: A NEWLY IDENTIFIED CD45-ASSOCIATED PROTEIN

RELATED APPLICATIONS

This application is a continuation-in-part of U.S. Ser. No. 08/004,199, entitled "pp32:A Newly Identified CD45-Associated Protein", filed Jan. 13, 1993, now abandoned, which is a file wrapper-continuation of U.S. Ser. No. 07/688,019, also entitled "pp32:A Newly Identified CD45-Associated Protein", filed. Apr. 19, 1991, now abandoned, both of which are hereby incorporated by reference.

FIELD OF THE INVENTION

This invention relates to a protein isolated from human T lymphocytes, methods for obtaining said protein and uses thereof an isolated nucleic acid molecule encoding said protein and uses thereof, and methods for obtaining inhibitors for said protein and uses thereof.

BACKGROUND OF THE INVENTION

Resting T lymphocytes can be activated in vitro by monoclonal antibodies against the T cell receptor complex (TCR-CD3) or against CD2, a 50kD glycoprotein. Activation of resting T lymphocytes by means of monoclonal antibodies leads to proliferation and differentiation and therefore mimics the action of the naturally occurring ligands for those receptors (antigen for the T cell receptor or the LFA-3 for CD2). The earliest step of T cell activation by either monoclonal antibodies or the natural ligands is a phosphorylation of a limited number of intracellular and transmembrane proteins (e.g. CD3 epsilon, CD3 zeta, CD4, CD8, CD45). Phosphorylation of proteins is thought to be mediated by intracellular protein kinases which are activated upon the binding of monoclonal antibodies or the appropriate ligands and which phosphorylate proteins either on tyrosine residues (protein tyrosine kinases) or on threonine- and/or serine residues (serine/threonine kinases). Alternatively, it is possible that constitutive dephosphorylation could be inhibited by T cell activation and could therefore be responsible for the increased abundance of phosphoproteins observed. During the last ten years, an increasing number of protein kinases has been identified, but only a very limited number of those are tyrosine kinases. These protein tyrosine kinases can be divided into two groups:

a) Tyrosine kinases that are also integral membrane proteins with extracellular ligand binding domains and intracellular catalytic domains (e.g. EGF receptor, PDGF receptor, insulin receptor); and b) Tyrosine kinases that do not possess an extracellular domain or membrane spanning region but associate with the inner leaf of the plasma membrane (e.g. $p56^{lck}$, $p60^{src}$, $p59^{fyn}$).

Protein tyrosine kinases of both groups are encoded by protooncogenes and may therefore play a role in the origin of malignant cell growth. Recent studies have shown that protein tyrosine kinases play a key role in the regulation of cell growth and differentiation. Tyrosine kinases can themselves be phosphorylated on serine, threonine and tyrosine. Recent studies have shown that the enzymatic activity of certain tyrosine kinases is partially dependent upon the degree of phosphorylation on tyrosine. This leads us to the conclusion that the activity of tyrosine kinases is at least partially regulated by tyrosine phosphatases.

The CD45 molecule, an integral membrane tyrosine phosphatase, is expressed on all hematopoietic cells, and seems to play a very important regulatory role during an immune response. This is shown by a number or T cell functions that are either increased or inhibited by monoclonal antibodies against the CD45 protein. However, it is not known whether those antibodies modulate the enzymatic activity of the molecule or which proteins are the natural substrates for CD45. $p56^{lck}$, a T cell specific tyrosine kinase that is associated with CD4, has been discussed as a possible substrate for CD45. However, no biochemical data are currently available that directly prove an association between CD45 and $p56^{lck}$. Therefore, no substrates for CD45 have been definitively identified.

Using unconventional immunoprecipitation techniques we have identified a potential substrate of CD45 which is the subject of this patent. The molecule is an intracellular protein with a relative apparent molecular weight of 32kD (SDS-PAGE) and a pI of 4.0 to 4.5. In resting T cells, this protein, "pp32", is constitutively phosphorylated on serine. Immunoprecipitation experiments with anti-CD45 monoclonal antibodies have shown that pp32 is specifically associated with CD45. Besides pp32, a tyrosine kinase coprecipitates with the CD45 molecule. The coprecipitated protein kinase is responsible for in vitro phosphorylation of pp32 on tyrosine residues. The tyrosine kinase has been identified by immunoprecipitation and subsequent peptide analysis as $p56^{lck}$. The ability of CD45 to use tyrosine phosphorylated pp32 as a substrate in vitro provides further evidence that an enzyme-substrate relationship exists for the two molecules in vivo. Detailed electrophoretic analysis or pp32 has subsequently shown that this protein exists (in resting T cells) in two isoforms (pp32 high and pp32 low). Both isoforms show rapid changes during the activation of T lymphocytes. The changes take place within 5 minutes after stimulation of resting T lymphocytes with monoclonal antibodies specific for CD2 or with Phorbol esters.

Based upon the amino acid sequences of peptide fragments of the isolated pp32 protein, a nucleic acid molecule encoding pp32 has been isolated.

SUMMARY OF THE INVENTION

The newly identified protein of this invention is characterized by (a) an apparent molecular weight of about 32 kD as determined by SDS-PAGE analysis, (b) an isoelectric point of about 4.0 to 4.5, and (c) coprecipitation with CD45. Various isoforms or derivatives of pp32 have also been identified, including pp32 phosphorylated on serine (in resting T cells). The invention provides an isolated pp32 protein. The protein may be phosphorylated or may be unphosphorylated. In one embodiment, the protein has an amino acid sequence shown in SEQ ID NO: 2.

The invention further provides an isolated nucleic acid molecule encoding a pp32 protein which can associate with CD45. In one embodiment, the nucleic acid molecule has a nucleotide sequence shown in SEQ ID NO: 1. Other aspects of the invention include recombinant expression vectors containing the nucleic acid molecules of the invention and host cells transfected with the recombinant expression vectors of the invention.

The invention provides a method for identifying agents which can upregulate or downregulate expression of pp32 in cells. Such agents can be used to modulate the expression of pp32 in cells. Other agents provided by the invention which can be used to modulate the expression and/or activity of pp32 in cells include antisense nucleic acid molecules, ribozymes and antibodies directed against pp32. The proteins and nucleic acids of the invention can further be used to identify and isolate proteins which interact with pp32 and map regions of interaction between pp32 and pp32-interactive proteins.

Compositions containing a therapeutically effective dose of pp32 or derivatives thereof in a pharmaceutically acceptable vehicle may be administered to patients for the treatment of diseases of the immune system such as rheumatoid arthritis, multiple sclerosis, diabetes, morbus crohn, systemic lupus erythematosus, graft rejection and allergies. Also, these proteins may be used to identify compounds which bind thereto, including compounds which bind and interfere with or prevent T cell activation.

BRIEF DESCRIPTION OF THE FIGURES

FIG. 2 shows pp32 in the two dimensional gel electrophoresis with a molecular weight of 32 kD and an isoelectric point of 4.0–4.5. At the upper end of the gel the CD45 molecule can be seen with a pI of about 5.5–6. The relatively faint spot at about 56kD most likely represents the protein kinase p56 lck.

FIG. 4 shows that in vitro phosphorylation of pp32 can be observed in the cell lines Jurkat and Laz-509 but not in t tPB-ALL and K562 as the latter cells do not express CD45. This suggests that the expression of CD45 is a prerequisite for the coprecipitation and subsequent in vitro phosphorylation of pp32. Lane D: Jurkat cells; Lane C: Laz-509 cells; Lane B: HPBALL cells; Lane A: K562 cells.

DETAILED DESCRIPTION OF THE INVENTION

Figure 1:
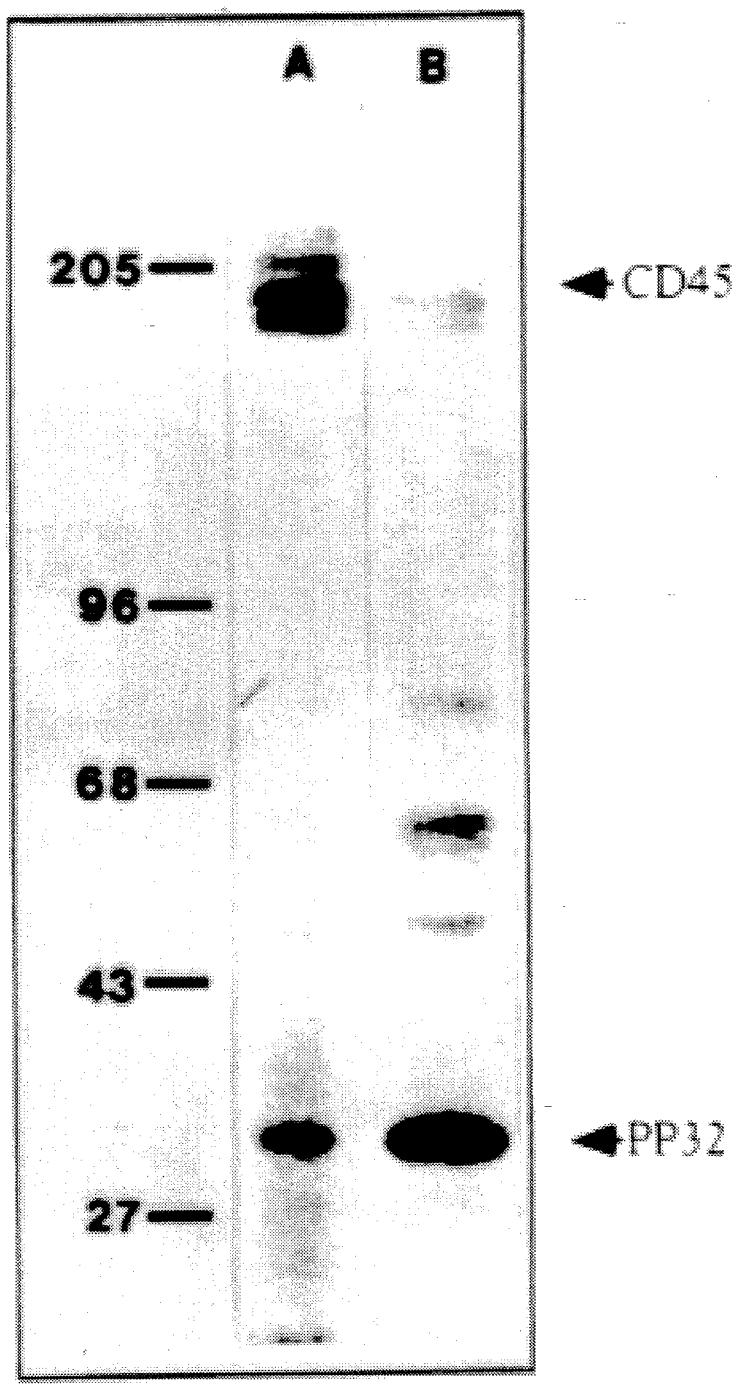
FIG. 1: Immunoprecipitation of CD45 associated pp32 FIG. 1. Lane A shows an immunoprecipitation experiment with anti-CD45 antibodies using cells that had been lysed with TRITON X-100. Four different CD45 bands with apparent molecular weights of 220, 205, 190, and 180 kD are visible. In addition, there is a faint band at 32 kD. Lane B shows the same CD45 immunoprecipitation obtained from cells solubilized with 1% digitonin. The 32kd band is much more pronounced under these lysis conditions. Lane A: CD45/1% Triton X-100; Lane B: CD45/1% digitonin.

The protein pp32 was detected by means of immunoprecipitation. T lymphocytes from peripheral blood (European J. of Immunology, 19, p. 337(1989)) were cultured for 12 hours (at 37° C. and 100% humidity) in phosphate free medium that had been supplemented with 32p orthophosphate. This treatment exchanges inorganic nonradioactive phosphate for radioactive phosphate in the intracellular pool. The cells were subsequently lysed at 4° C. for 45 minutes and the cell nuclei removed by centrifugation. Lysates were preabsorbed for 30 minutes with CNBr activated protein A sepharose to which an irrelevant monoclonal antibody (IgGl; 6 μg/ml) had been bound. It was followed by the immunoprecipitation with an anti-CD45 monoclonal antibody (Gap 8.3 from hybridoma HB 12, ATCC) and the precipitate was separated by means of electrophoresis. It was shown that the pp32 specifically coprecipitates with the anti-CD45 monoclonal antibody. Neither the isotype of the monoclonal antibody nor the isoform of the CD45 that is being recognized seems to play a role. The method for kinasing the sample in vitro is similar to the technique for immunoprecipitation of in vivo labeled material.

To determine the isoelectric point, the precipitates were separated from the sepharose beads by means of electroelution. Subsequently the eluted proteins were precipitated with acetone. The acetone was evaporated and the proteins were washed and dried. The pI determination was performed by two dimensional gel electrophoresis according to O'Farrel. Pp32 was shown to have an isoelectric point of 4.0 to 4.5.

For the phosphoamino acid analysis, CD45 immunoprecipitates that had been obtained from digitonin lysed T lymphocytes were separated electrophoretically and the location of pp32 was determined by means of autoradiography. Subsequently pp32 was cut out of the gel, rehydrated, electroeluted, precipitated with acetone, hydrolysed and dried. The phosphoamino acid analysis was then performed by two dimensional thin layer chromatography on cellulose plates (Merck). It was observed that in vivo labeled pp32 from unstimulated cells was predominantly phosphorylated on serine. In contrast, where the CD45 immunoprecipitates were kinased in vitro the same protein was exclusively phosphorylated on tyrosine residues. This requires the presence of a tyrosine kinase as for example p56$^{lck}$. In vitro experiments showed that active CD45 is able to dephosphorylate in vitro labeled pp32.

The pp32 protein of this invention can be purified in larger amounts using otherwise conventional methods. For example, approximately $10^{10}$–$10^{15}$ of CD45 positive T cells, preferably human such as the Jurkat T cell line, are produced by cell culture using conventional methods and materials, including a conventional culture medium. The cells are then separated from the culture medium by centrifugation (pelleting) or any other convenient methods, rinsed as desired to remove residual media or media components, and then lysed in an appropriate volume of Lysis-buffer supplemented with 1% digitonin. The lysate is precleared several times with an appropriate volume (e.g. ~250 µl/$10^8$ cells) of packed CNBr Sepharose beads coupled with an unrelated mAb. The material is then absorbed with an appropriate quantity of anti-CD45 coupled beads. The beads are washed several times in a large volume of Lysis buffer and a portion removed for in vitro kinasing (e.g. 100 µl of packed beads). The kinased material is mixed with the unlabeled material to act as a tracer for later identification. A preparative nonreducing 10% SDS-PAGE gel would be run on the material to avoid contamination with low molecular weight proteins (e.g. light chains of the precipitating CD45 mAb). The position of pp32 may be identified by autoradiography, the appropriate band excised from the SDS gel and the protein electroeluted using an electroelution chamber (Schleicher and Schuell, see protocol for two dimensional gel electrophoresis). pp32 may be precipitated with acetone and dissolved in loading buffer for two dimensional gel electrophoresis. The precipitate may then be resolved in an isoelectric focusing system separating by pI in the first dimension and by molecular weight in the second dimension (reducing 10% SDS-PAGE). The position of pp32 may be identified by staining the gel with Coomassie blue. In addition, the position of pp32 can be checked by means of autoradiography. Thus the material may be obtained, purified, eluted and sequenced.

Alternatively, CD45 and the associated pp32 protein could be removed from the cell lysate as a complex, e.g. by immunoprecipitation or immunoaffinity chromatography using immobilized (or immobilizable or otherwise separable) antibody against CD45. For instance, an CD45 monoclonal antibody (GAP 8.3) previously bound to protein A-sepharose beads can be used to immunoprecipitate the CD45 complex containing pp32 protein. The beads would then be separated from the remaining components of the cell lysate and washed, e.g. in lysis buffer, to remove any extraneous materials including non-CD45-associated constituents of the cell lysate. The separated beads bearing the pp32 protein would then be treated to release the pp32 protein which may then be separately recovered. For instance, the beads may be resuspended in a TRITON X-100 containing buffer to release the bound pp32 into solution. Alternatively, the beads may be treated with 6M guanidine to release bound proteins. Whichever method is chosen, the pp32 protein may be separated from other proteins in the solution by conventional methods such as reverse phase HPLC (which can be relied upon to achieve purity levels typically in excess of 95%) or by SDS-PAGE. Such methods should provide sufficiently purified samples of pp32 protein to permit further characterization of the protein, including amino acid sequencing — whether pp32 was purified by HPLC or cut from a nitrocellulose membrane to which it had been blotted from a polyacrylamide gel.

The fact that this protein can now be obtained in pure form (preferably at least about 90% free from other human proteins with which it is associated in nature, and more preferably at least about 95% free) by the above-described methods now makes it possible for one to apply conventional methods to elucidate the amino acid composition and sequence of the proteins as mentioned above; and to produce antisera or monoclonal antibodies capable of specifically binding to p32, to recover and further purify the pp32 protein, if desired, by adaptation of otherwise conventional methods including reverse phase HPLC and/or other chromatographic methods, including immunoaffinity techniques, for instance using specific anti-pp32 antibodies. Such antibodies may also be used to immunopurify proteins associated with pp32. In such methods pp32 and associated protein(s) would be separated from other materials by virtue of binding to the anti-pp32 antibodies (which may be immobilized), the bound materials would then be washed to remove contaminants, i.e., materials not specifically associated with the pp32 protein or with proteins specifically associated with pp32, and the molecules associated with the pp32 may then be separately released from the pp32, for example by altering the ionic strength of the buffer, and then removing materials as released from the association.

This invention thus identifies for the first time the existence of a novel component of the T cell cellular machinery. Given the information disclosed herein, the protein can now be obtained for the first time and in purified form, e.g. from natural sources (such as cultured CD45+ T cells). Compositions containing pp32 protein can be used to produce specific antibodies capable of recognizing and binding to p32. pp32 proteins can be purified directly by immunoaffinity methods using such antibodies rather than indirectly with CD45 antibodies as discussed previously. That may be especially desirable in cases where there may be a molar excess of pp32 relative to CD45, e.g. in the case of heterologous overexpression of a DNA sequence encoding pp32 or a mutein thereof. In addition, pp32 antibodies can be used to screen or identify cells which produce higher levels of p32. Such cells, including perhaps genetically engineered host cells which overexpress pp32 or muteins thereof can be used to screen molecules to identify those which act as modulators of T cell activation.

The ability to isolate pp32 protein allowed for the determination of the amino acid sequences of several peptide fragments of the protein. These peptide fragments included an amino-terminal fragment, tryptic fragments and V8 protease fragments. Based upon the amino acid sequences of these peptide fragments, degenerate oligonucleotide primers could be designed which are complementary to nucleic acid encoding pp32. These primers were used in polymerase chain reactions to amplify small fragments of the pp32 cDNA. A small pp32 cDNA fragment was then used a probe to screen a human cDNA library to obtain a full-length cDNA encoding pp32. The nucleotide sequence of a pp32 cDNA is shown in SEQ ID NO: 1. The predicted amino acid sequence of the protein encoded by this cDNA is shown in SEQ ID NO: 2. In vitro translation of the isolated cDNA produced a protein which migrated in polyacrylamide gels at a molecular weight of 32 kD. The in vitro translated protein was immunoreactive with an antiserum raised against isolated pp32 protein from Jurkat cells. The amino acid sequence of the amino-terminal peptide fragment of pp32 begins at amino acid position 21 of SEQ ID NO: 2, which likely indicates that the first 20 amino acids of the predicted protein correspond to a signal sequence. Furthermore, there is a stretch of hydrophobic amino acid residues close to the N-terminal end of the mature protein, consistent with pp32 being a membrane-bound protein.

The invention provides an isolated nucleic acid molecule encoding a pp32 protein which associates with CD45. The term "isolated" as used herein refers to a nucleic acid molecule substantially free of cellular material or culture medium when produced by recombinant DNA techniques, or chemical precursors or other chemicals when chemically synthesized. An "isolated" nucleic acid molecule is also free of sequences which naturally flank the nucleic acid (i.e., sequences located at the 5' and 3' ends of the nucleic acid) in the organism from which the nucleic acid is derived. The term "nucleic acid" is intended to include DNA and RNA and can be either double stranded or single stranded. In one embodiment, the isolated nucleic acid molecule is a cDNA. Preferably, the pp32 protein encoded by the nucleic acid is a human protein. In one embodiment, the nucleic acid encoding a human pp32 protein comprises a nucleotide sequence shown in SEQ ID NO: 1. In another embodiment, the nucleic acid encoding a human pp32 protein comprises a coding region of the nucleotide sequence shown in SEQ ID NO: 1.

An isolated nucleic acid of the invention can be isolated using standard molecular biology techniques. For example, a nucleic acid molecule encoding a pp32 protein can be amplified from genomic DNA or cDNA by the polymerase chain reaction using oligonucleotide primers designed based upon the nucleotide sequence shown in SEQ ID NO: 1. Alternatively, a nucleic acid molecule encoding a pp32 protein can be isolated by screening a cDNA or genomic DNA library with a probe containing all or part of the nucleotide sequence shown in SEQ ID NO: 1. A nucleic acid of the invention (for instance an oligonucleotide) can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

It will be appreciated by those skilled in the art that nucleic acids encoding a pp32 protein which associates with CD45 which have a nucleotide sequences other than those provided by the invention can be isolated or synthesized by standard techniques. For example, an isolated nucleic acid encoding a pp32 protein can have a different nucleotide sequence than that described herein due to degeneracy in the genetic code. Such nucleic acids encode functionally equivalent proteins but differ in sequence from the sequences described herein due to degeneracy in the genetic code. For example, a number of amino acids are designated by more than one triplet. Codons that specify the same amino acid, or synonyms (for example, CAU and CAC are synonyms for histidine) may occur due to degeneracy in the genetic code. As one example, DNA sequence polymorphisms within the nucleotide sequence of a pp32 protein (especially those within the third base of a codon) may result in "silent" mutations in the DNA which do not affect the amino acid encoded. Isolated nucleic acids encoding a human pp32 protein having a nucleotide sequence which differs from that provided herein (i.e., SEQ ID NO: 1) due to degeneracy of the genetic code are considered to be within the scope of the invention. Furthermore, it is expected that DNA sequence polymorphisms that do lead to changes in the amino acid sequences of a pp32 protein will exist within a population. It will be appreciated by one skilled in the art that these variations in one or more nucleotides (up to about 3–4% of the nucleotides) of the nucleic acids encoding proteins having the properties of pp32 (e.g., ability to associate with CD45) may exist among individuals within a population due to natural allelic variation. Any and all such nucleotide variations and resulting amino acid polymorphisms are within the scope of the invention.

The isolated nucleic acids of the invention are useful for constructing nucleotide probes for use in the detection of nucleotide sequences in biological materials, such as cell extracts, or directly in cells (e.g., by in situ hybridization). A nucleotide probe can be labeled with a radioactive element which provides for an adequate signal as a means for detection and has sufficient half-life to be useful for detection, such as $^{32}P$, $^{3}H$, $^{14}C$ or the like. Other materials which can be used to label the probe include antigens that are recognized by a specific labeled antibody, fluorescent compounds, enzymes and chemiluminescent compounds. An appropriate label can be selected with regard to the rate of hybridization and binding of the probe to the nucleotide sequence to be detected and the amount of nucleotide available for hybridization. The isolated nucleic acids of the invention, or oligonucleotide fragments thereof, can be used as suitable probes for a variety of hybridization procedures well known to those skilled in the art. The isolated nucleic acids of the invention enable one to determine whether a cell expresses an mRNA transcript encoding a pp32 protein. For example, mRNA can be prepared from a sample of cells to be examined and the mRNA can be hybridized to an isolated nucleic acid encompassing a nucleotide sequence comprising all or a portion of SEQ ID NO: 1. Furthermore, the isolated nucleic acids of the invention can be used to design oligonucleotide primers, e.g. PCR primers, which allow one to detect the expression of a pp32 mRNA transcript in a cell.

The isolated nucleic acid molecules of the invention can be used in assays to screen for agents which upregulate or downregulate expression of pp32 mRNA transcripts. The invention provides a method for identifying an agent which can upregulate or downregulate expression of a pp32 mRNA. The method involves contacting a cell which expresses or can be induced to express pp32 with an agent to be tested and detecting expression of pp32 mRNA in the cell in the presence and absence of the agent. A preferred cell type for use in the method of the invention is a T lymphocyte. The term "upregulates" encompasses inducing the expression of pp32 mRNA in a cell which does not constitutively express pp32 or increasing the level of expression of pp32 mRNA in a cell which already expresses pp32. The term "downregulates" encompasses decreasing or eliminating expression of pp32 mRNA in a cell which already expresses pp32. The term "agent" is intended to include molecules which trigger an upregulatory or downregulatory response in a cell. For example, an agent can be a small organic molecule, a biological response modifier (e.g., a cytokine) or a molecule which can crosslink surface structures on the cell (e.g., an antibody). Expression of pp32 mRNA in a cell can be detected, for example, by reverse transcribing mRNA from the cell and using the cDNA thus obtained as a template in PCR reactions utilizing PCR primers which can detect pp32 cDNA (i.e., PCR primers designed based upon the nucleotide sequence of a pp32 cDNA, e.g., SEQ ID NO: 1). Alternatively, pp32 mRNA can be detected by standard hybridization techniques (e.g., Northern hybridization; RNase protection) using probes encompassing all or part of a nucleotide sequence encoding a pp32 protein (e.g., all or part of SEQ ID NO: 1 ). An agent which upregulates or downregulates expression of a pp32 mRNA in a cell, identified by the method of the invention, can be used to modulate the level of expression of pp32 in a cell.

Another type of agent which can be used to modulate the expression of pp32 in a cell is an antisense nucleic acid molecule. An antisense nucleic acid molecule which is complementary to a nucleic acid molecule encoding pp32 can be designed based upon the isolated nucleic acid molecules encoding pp32 provided by the invention. An antisense nucleic acid molecule can comprise a nucleotide sequence which is complementary to a coding strand of a nucleic acid, e.g. complementary to an mRNA sequence, constructed according to the rules of Watson and Crick base pairing, and can hydrogen bond to the coding strand of the nucleic acid. The antisense sequence complementary to a sequence of an mRNA can be complementary to a sequence/ bund in the coding region of the mRNA or can be complementary to a 5' or 3' untranslated region of the mRNA. Furthermore, an antisense nucleic acid can be complementary in sequence to a regulatory region of the gene encoding the mRNA, for instance a transcription initiation sequence or regulatory element. Preferably, an antisense nucleic acid complementary to a region preceding or spanning the initiation codon or in the 3' untranslated region of an mRNA is used. An antisense nucleic acid can be designed based upon the nucleotide sequence shown in SEQ ID NO: 1. A nucleic acid is designed which has a sequence complementary to a sequence of the coding or untranslated region of the shown nucleic acid. Alternatively, an antisense nucleic acid can be designed based upon sequences of a pp32 gene, which can be identified by screening a genomic DNA library with an isolated nucleic acid of the invention. For example, the sequence of an important regulatory element can be determined by standard techniques and a sequence which is antisense to the regulatory element can be designed.

The antisense nucleic acids and oligonucleotides of the invention can be constructed using chemical synthesis and enzymatic ligation reactions using procedures known in the art. The antisense nucleic acid or oligonucleotide can be chemically synthesized using naturally occurring nucleotides or variously modified nucleotides designed to increase the biological stability of the molecules or to increase the physical stability of the duplex formed between the antisense and sense nucleic acids e.g. phosphorothioate derivatives and acridine substituted nucleotides can be used. Alternatively, the antisense nucleic acids and oligonucleotides can be produced biologically using an expression vector into which a nucleic acid has been subcloned in an antisense orientation (i.e. nucleic acid transcribed from the inserted nucleic acid will be of an antisense orientation to a target nucleic acid of interest). The antisense expression vector is introduced into cells in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews — Trends in Genetics, Vol. 1 (1)1986

The nucleic acids of the invention can further be used to design ribozymes which are capable of cleaving a single-stranded nucleic acid encoding a pp32 protein, such as a pp32 mRNA transcript. A catalytic RNA (ribozyme) having ribonuclease activity can be designed which has specificity for an mRNA encoding pp32 based upon the sequence of a nucleic acid of the invention (e.g., SEQ ID NO: 1 ). For example, a derivative of a Tetrahymena L-19 IVS RNA can be constructed in which the base sequence of the active site is complementary to the base sequence to be cleaved in a pp32-encoding mRNA. See for example Cech et al. U.S. Pat. No. 4,987,071; Cech et al. U.S. Pat. No. 5,116,742. Alternatively, a nucleic acid of the invention could be used to select a catalytic RNA having a specific ribonuclease activity from a pool of RNA molecules. See for example Bartel, D. and Szostak, J. W. Science 261,1411–1418 (1993).

An isolated nucleic acid molecule of the invention encoding a pp32 protein can be incorporated in a known manner into a recombinant expression vector which ensures good expression of the encoded protein or portion thereof. A recombinant expression vector is suitable for transformation of a host cell, which means that the recombinant expression vector contains a nucleic acid or an oligonucleotide fragment thereof of the invention and a regulatory sequence, selected on the basis of the host cells to be used for expression, which is operatively linked to the nucleic acid or oligonucleotide fragment. Operatively linked is intended to mean that the nucleic acid is linked to a regulatory sequence in a manner which allows expression of the nucleic acid. Regulatory sequences are art-recognized and are selected to direct expression of the desired protein in an appropriate host cell. Accordingly, the term regulatory sequence includes promoters enhancers and other expression control elements. Such regulatory sequences are known to those skilled in the art or one described in Goeddel, *Gene Expression Technology: Methods in Enzymology* 185, Academic Press, San Diego, CA (1990) can be used. It should be understood that the design of the expression vector may depend on such factors as the choice of the host cell to be transfected and/or the type of protein desired to be expressed. Such expression vectors can be used to transfect cells to thereby produce proteins or peptides encoded by nucleic acids as described herein.

The recombinant expression vectors of the invention can be designed for expression of encoded proteins in prokaryotic or eukaryotic cells. For example, proteins can be expressed in bacterial cells such as *E. coli*, insect cells (using baculovirus), yeast cells or mammalian cells. Other suitable host cells can be found in Goeddel, *Gene Expression Technology: Methods in Enzymology* 185, Academic Press, San Diego, CA (1990).

Expression in prokaryotes is most often carried out in *E. coli* with vectors containing constitutive or inducible promoters directing the expression of either fusion or non-fusion proteins. Fusion vectors add a number of amino acids usually to the amino terminus of the expressed target gene. Such fusion vectors typically serve three purposes: 1) to increase expression of recombinant protein; 2) to increase the solubility of the target recombinant protein; and 3) to aid in the purification of the target recombinant protein by acting as a ligand in affinity purification. Often, in fusion expression vectors, a proteolytic cleavage site is introduced at the junction of the fusion moiety and the target recombinant protein to enable separation of the target recombinant protein from the fusion moiety subsequent to purification of the fusion protein. Such enzymes, and their cognate recognition sequences, include Factor Xa, thrombin and enterokinase. Typical fusion expression vectors include pGEX (Amrad Corp., Melbourne, Australia), pMAL (New England Biolabs, Beverly, MA) and pRIT5 (Pharmacia, Piscataway, NJ) which fuse glutathione S-tranferase, maltose E binding protein, or protein A, respectively, to the target recombinant protein.

Inducible non-fusion expression vectors include pTrc (Antann et al., (1988) Gene 69:301–315) and the pET series of vectors (Studier et āl., *Gene Expression Technology: Methods in Enzymology* 185, Academic Press, San Diego, California (1990) 60–89). In pTrc, target gene expression relies on host RNA polymerase transcription from a hybrid trp-lac fusion promoter. In pET vectors, expression of inserted target genes relies on transcription from the T7 gn10-lac 0 fusion promoter mediated by a coexpressed viral RNA polymerase (T7 gnl ). This viral polymerase is supplied by host strains BL2 I(DE3) or HMS174(DE3) front a resident λ prophage harboring a T7 gnl under the transcriptional control of the lacUV 5 promoter.

One strategy to maximize recombinant protein expression in E. coli is to express the protein in a host bacteria with an impaired capacity to proteolytically cleave the recombinant protein (Gottesman, S., Gene Expression Technology: Methods in Enzymology 185, Academic Press, San Diego, Calif. (1990) 119–128). Another strategy is to alter the nucleic acid sequence of the nucleic acid to be inserted into an expression vector (e.g. a nucleic acid encoding a pp32 protein) so that the individual codons for each amino acid would be those preferentially utilized in highly expressed E. coli proteins (Wada et al., (1992) Nuc. Acids Res. 90:2111–2118). Such alteration of nucleic acid sequences of the invention could be carried out by standard DNA synthesis techniques.

Examples of vectors for expression in yeast S. cerivisae include pYepSecl (Baldari. et al., (1987) Embo J. 6:229–234), pMFa (Kurjan and Herskowitz, (1982) Cell 30:933–943), pJRY88 (Schultz et al., (1987) Gene 54:113–123), and pYES2 (Invitrogen Corporation, San Diego, Calif.).

Baculovirus vectors available for expression of proteins in cultured insect cells (SF 9 cells) include the pAc series (Smith etal., (1983) Mol. Cell Biol. 3:2156–2165) and the pVL series (Lucklow, V. A., and Summers, M. D., (1989) Virology 170:31–39).

Expression of a pp32 protein in mammalian cells is accomplished using a mammalian expression vector. Examples of mammalian expression vectors include pCDM8 (Seed, B., (1987) Nature 329:840) and pMT2PC (Kaufman et al. (1987), EMBO J 6:187–195). When used in mammalian cells, the expression vector's control functions are often provided by viral material. For example, commonly used promoters are derived from polyoma, Adenovirus 2, cytomegalovirus and most frequently, Simian Virus 40. In one embodiment, the recombinant expression vector is capable of directing expression of the nucleic acid preferentially in a particular cell type. This means that the expression vector's control functions are provided by regulatory sequences which allow for preferential expression of a nucleic acid contained in the vector in a particular cell type, thereby allowing for tissue or cell-type specific expression of an encoded protein.

The recombinant expression vector of the invention can be a plasmid. Alternatively, the recombinant expression vector of the invention can be a virus, or portion thereof, which allows for expression of a nucleic acid introduced into the viral nucleic acid. For example, replication defective retroviruses, adenoviruses and adeno-associated viruses can be used.

The invention further provides a recombinant expression vector comprising a DNA molecule of the invention cloned into the expression vector in an antisense orientation. That is, the DNA molecule is operatively linked to a regulatory sequence in a manner which allows for expression, by transcription of the DNA molecule, of an RNA molecule which is antisense to the nucleotide sequence of SEQ ID NO: 1. Regulatory sequences operatively linked to the antisense nucleic acid can be chosen which direct the continuous expression of the antisense RNA molecule in a variety of cell types, for instance a viral promoter and/or enhancer, or regulatory sequences can be chosen which direct tissue or cell type specific expression of antisense RNA.

The recombinant expression vectors of the invention can be used to make a transformant host cell including the recombinant expression vector. The term "transformant host cell" is intended to include prokaryotic and eukaryotic cell which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

The number of host cells transfected with a recombinant expression vector of the invention by techniques such as those described above will depend upon the type of recombinant expression vector used and the type of transfection technique used. Typically, plasmid vectors introduced into mammalian cells are integrated into host cell DNA at only a low frequency. In order to identify these integrants, a gene that contains a selectable marker (i.e., resistance to antibiotics) can be introduced into the host cells along with the gene of interest. Preferred selectable markers include those which confer resistance to certain drugs, such as G418 and hygromycin. Selectable markers can be introduced on a separate vector (e.g., plasmid) from the nucleic acid of interest or, preferably, are introduced on the same vector (e.g., plasmid). Host cells transformed with one or more recombinant expression vectors containing a nucleic acid of the invention and a gene for a selectable marker can be identified by selecting for cells using the selectable marker. For example, if the selectable marker encoded a gene conferring neomycin resistance, transformant cells can be selected with G418. Cells that have incorporated the selectable marker gene will survive, while the other cells die.

The invention provides an isolated pp32 protein which can associate with CD45. The term "isolated" refers to a protein substantially free of cellular material or culture medium when produced by recombinant DNA techniques, or chemical precursors or other chemicals when chemically synthesized. In one embodiment the pp32 protein is a human protein. When expressed in a non-human cell, e.g., using a recombinant expression vector introduced onto a non-human cell an isolated human pp32 protein can be obtained which is free of other human proteins. Preferably, a human pp32 protein comprises an amino acid sequence shown in SEQ ID NO: 2. Proteins which have substantial sequence homology to the amino acid sequence of SEQ ID NO: 2 are also encompassed by the invention. The term "sequences having substantial sequence homology" means those amino acid sequences which have slight or inconsequential sequence variations from the amino acid sequence disclosed in SEQ ID NO: 2, (i.e. a protein with the variant amino acid sequence functions in substantially the same manner as a protein with the amino acid sequence of SEQ ID NO: 2). The variations may be attributable to local mutations or structural modifications. It is expected that substitutions or alterations can be made in various regions of the amino acid sequence without affecting protein function, e.g., the ability of the protein to associate with CD45 and to be a substrate for CD45. The term "pp32 protein" is intended to include fragments, mutants or variants of native pp32 that retain the ability to associate with CD45. A "fragment" of a pp32 protein is defined as a portion of pp32 which retains the ability to associate with CD45. For example, a fragment of pp32 has fewer amino acid residues than the entire protein. A "mutant" is defined as a pp32 protein having a structural change which does not eliminate the ability of the protein to associate with CD45. For example, a mutant of pp32 may have a change (e.g., subsitution, deletion or addition) in one or more amino acid residues of the protein. A "variant" is defined as a pp32 protein having a modification which does not affect the ability of the protein to associate with CD45. For example, a variant of pp32 may have altered glycosylation or may be a chimeric protein of pp32 and another protein. Additionally, immunogenic portions of pp32 proteins are within the scope of the invention. An immunogenic portion is typically of at least about eight amino acids in length and can be predicted using algorithms, known in the art, which predict which regions of a protein are located on the surface of the protein. Additionally, peptide fragments of pp32 provided by the invention (see Example 9) can be used to generate anti-peptide antibodies. For example, an N-terminal peptide fragment encompassing amino acid positions 21–30 of SEQ ID NO: 2 or an internal peptide fragment encompassing amino acid position 175–195 of SEQ ID NO: 2 can be used as an immunogenic peptide.

A pp32 protein, or isoform or portion thereof, of the invention can be isolated by expression in a suitable host cell using techniques known in the art. Suitable host cells include prokaryotic or eukaryotic organisms or cell lines, for example, yeast, *E. coli* and insect cells. The recombinant expression vectors of the invention, described above, can be used to express pp32 in a host cell in order to isolate the protein. The invention provides a method of preparing an isolated protein of the invention comprising introducing into a host cell a recombinant nucleic acid encoding the protein, allowing the protein to be expressed in the host cell and isolating the protein. Preferably, the recombinant nucleic acid is a recombinant expression vector. Proteins can be isolated from a host cell expressing the protein according to standard procedures of the art, including ammonium sulfite precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology*, 22, 233–577 (1971)). Alternatively, a pp32 protein, or portion(s) thereof; of the invention can be prepared by chemical synthesis using techniques well known in the chemistry of proteins such as solid phase synthesis (Merrifield, 1964, *J. Am. Chem. Assoc.* 85:2149–2154) or synthesis in homogeneous solution (Houbenweyl, 1987, Methods of Organic Chemistry, ed. E. Wansch, Vol. 15 I and II, Thieme, Stuttgart). Depending on its method of preparation, a pp32 protein of the invention may be phosphorylated or not phosphorylated. For example, pp32 isolated from resting cells (e.g., resting Jurkat cells) is phosphorylated on serine. Alternatively, pp32 isolated from activated cells, isolated by recombinant expression of the protein in a prokaryotic cell (e.g., *E. coli*) or chemically synthesized may not be phosphorylated.

An isolated pp32 protein (or peptide fragment thereof), obtained by purification of the native protein, recombinant expression of the protein or chemical synthesis, can be used to produce antibodies directed against the pp32 protein. For example, the protein shown in SEQ ID NO: 2, or an immunogenic portion thereof, can be used generate antibodies reactive with (i.e., capable of binding to) the protein. Conventional methods can be used to prepare the antibodies. For example, a mammal, (e.g., a mouse, hamster, or rabbit) can be immunized with an immunogenic form of the protein or peptide which elicits an antibody response in the mammal. Techniques for conferring immunogenicity on a protein include conjugation to carriers or other techniques well known in the art. For example, the protein can be administered in the presence of adjuvant. The progress of immunization can be monitored by detection of antibody filters in plasma or serum. Standard ELISA or other immunoassay can be used with the immunogen as antigen to assess the levels of antibodies. Following immunization, antisera can be obtained and, if desired, polyclonal antibodies isolated from the sera.

In one embodiment, the antibody which binds a pp32 protein is a monoclonal antibody. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (Nature 256, 495–497 (1975)) as well as other techniques such as the human B-cell hybridoma technique (Kozbor et al., *Immunol. Today* 4, 72 (1983)), the EBV-hybridoma technique to produce human monoclonal antibodies (Cole et al. *Monoclonal Antibodies in Cancer Therapy* (1985) Allen R. Bliss, Inc., pages 77–96), and screening of combinatorial antibody libraries (Iluse et al., *Science* 246, 1275 (1989)). Hybridoma cells can be screened immunochemically for production of antibodies specifically reactive with the protein or portion thereof and monoclonal antibodies isolated.

The term antibody as used herein is intended to include fragments thereof which are also specifically reactive with pp32. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

Chimeric and humanized antibodies are also within the scope of the invention. It is expected that chimeric and humanized antibodies would be less immunogenic in a human subject than the corresponding non-chimeric antibody. A variety of approaches for making chimeric antibodies, comprising for example a non-human variable region and a human constant region, have been described. See, for example, Morrison et al., *Proc. Natl. Acad. Sci. U.S.A.* 81,6851 (1985); Takeda et al., *Nature* 314,452(1985), Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B. Additonally, a chimeric antibody can be further "humanized" such that parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., *Proc. Natl. Acad Sci. U.S.A.*, 80, 7308–7312 (1983); Kozbor et al., *Immunology Today*, 4, 7279 (1983); Olsson et al., *Meth. Enzymol.*, 92, 3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain.

Another method of generating specific antibodies, or antibody fragments, reactive against an alternative cytoplasmic domain of the invention is to screen phage expression libraries encoding immunoglobulin genes, or portions thereof, with a protein of the invention, or peptide fragment thereof (e.g., with all or a portion of a protein with the amino acid sequence of SEQ ID NO: 2). For example, complete Fab fragments, $V_H$ regions and V-region derivatives can be expressed in bacteria using phage expression libraries. See for example Ward et al., *Nature* 341,544–546: (1989); Huse et al., *Science* 246, 1275–1281 (1989); and McCafferty et al. *Nature* 348, 552–554 (1990).

An antibody of the invention can be used to detect a pp32 protein, e.g. in cells or cell extracts or other biological preparations which can contain pp32. An antibody can be labeled with a detectable substance to allow detection of an antibody/antigen complex. Suitable detectable substances with which to label an antibody include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

The isolated nucleic acids of the invention can further be used to create a non-human transgenic animal. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. Accordingly, the invention provides a non-human transgenic animal which contains cells transfected to express pp32 protein. Preferably, the non-human animal is a mouse. A transgenic animal can be created, for example, by introducing a nucleic acid encoding the protein (typically linked to appropriate regulatory elements, such as a tissue-specific enhancer) into the male pronuclei of a fertilized oocyte, e.g., by microinjection, and allowing the oocyte to develop in a pseudopregnant female foster animal. For example, a transgenic animal (e.g., a mouse) which expresses a human pp32 protein can be made using the isolated nucleic acid shown in SEQ ID NO: 1. Intronic sequences and polyadenylation signals can also be included in the transgene to increase the efficiency of expression of the transgene. These isolated nucleic acids can be linked to regulatory sequences which direct the expression of the encoded protein in one or more particular cell types. Methods for generating transgenic animals, particularly animals such as mice, have become conventional in the art and are described, for example, in U.S. Pat. Nos. 4,736,866 and 4,870,009 and Hogan, B. et al., (1986) A Laboratory Manual, Cold Spring Harbor, New York, Cold Spring Harbor Laboratory. A transgenic founder animal can be used to breed additional animals carrying the transgene.

The isolated nucleic acids of the invention can further be used to create a non-human "knock-out" animal. The term "knock-out animal" as used herein is intended to describe an animal containing a gene which has been modified by homologous recombination. The homologous recombination event may completely disrupt the gene such that a functional gene product can no longer be produced (hence the name "knock-out") or the homologous recombination event may modify the gene such that an altered, although still functional, gene product is produced. For example, an isolated nucleic acids of the invention can be used to create an animal in which the gene encoding pp32 is disrupted. Preferably, the non-human animal is a mouse. To create an animal with homologously recombined nucleic acid, a vector is prepared which contains the DNA which is to replace the endogenous DNA flanked by DNA homologous to endogenous DNA (see for example Thomas, K. R. and Capecchi, M. R. (1987) *Cell* 51:503). The vector is introduced into an embryonal stem cell line (e.g., by electroporation) and cells in which the introduced DNA has homologously recombined with the endogenous DNA are selected (see for example Li, E. et al. (1992) *Cell* 69:915). The selected cells are then injected into a blastocyst of an animal (e.g., a mouse) to form aggregation chimeras (see for example Bradley, A. in Teratocarcinomas and Embryonic Stem Cells. A Practical Approach, E. J. Robertson, ed. (IRL, Oxford, 1987) pp. 113–152). A chimeric embryo can then be implanted into a suitable pseudopregnant female foster animal and the embryo brought to term. Progeny harbouring the homologously recombined DNA in their germ cells can be used to breed animals in which all cells of the animal contain the homologously recombined DNA.

Besides cell/cell interaction molecules which exist at the cell surface of immunocompetent cells, e.g. T lymphocytes, a second set of potential targets for immunotherapy exist at the level of the signal transduction pathways responsible for transmission of messages from the cell membrane to the nucleus. In this regard, many transmembrane molecules expressed at the cell surface serve as receptor structures which transmit external signals into the genetic machinery in the cellular nucleus. Some cytosolic molecules represent components that are associated with the inner leaf of the plasma membrane and are linked to cell surface receptors. The former are modified in their function following engagement of the respective receptor structure to which they are linked. One mechanism of modulating protein function is achieved by adding or removing phosphate residues (phosphorylation/dephosphorylation) by respective enzymes, namely protein kinases and protein phosphatases. The initial regulation of cellular reactions occurs at the level of this critical balance between phosphorylation and dephosphorylation. Therefore, it is possible to utilize such intracellular molecules as targets for immune modulation, e.g. with the goal of downregulating immune responses in human diseases which are associated with or even due to enhanced reactivity of the immune system (i.e. chronic inflammatory disease, autoimmune disease, transplant rejection, allergy). Moreover, it is possible that abnormalities of such proteins, e.g. due to mutation or, alternatively, abnormal regulation of these molecules due to alteration in their respective enzymes, could lead to aberrant/malignant growth behavior. Therefore, such molecules are also potential targets for cytostatic therapy of malignant tumors.

The isolated nucleic acids and proteins of the invention can be used to identify and isolate molecules which interact with a pp32 protein. Regions within pp32 and/or within a pp32-interactive protein which are involved in the interaction between the two molecules can also be mapped. For example, an isolated nucleic acid of the invention can be cloned into an expression vector that can be used in an interaction trap assay such as that described in Gyuris, J. et al. (1993) *Cell* 791–803. A pp32 protein can be used as "bait" to select other proteins which interact with pp32 from an expression library. Additionally, a similar assay system can be used to map regions within pp32 important for interactions with known pp32-interactive proteins (e.g. CD45, p56lck) or to be identified pp32-interactive proteins. Likewise, regions in other proteins important for interaction with pp32 can be so mapped. Regions so identified can be mutated or targeted with an inhibitory agent (e.g., antibody or peptide) to disrupt interactions between pp32 and pp32-interactive proteins.

This invention is further illustrated by the following examples which should not be construed as limiting. The contents of all references and published patents and patent applications cited throughout the application are hereby incorporated by reference.

Example 1. Immunoprecipitation of CD45 Associated pp32

$4 \times 10^7$ resting human T cells were washed two times in phosphate free medium (distilled water, 2.5% Idepes-Buffer (GIBCO), 2% nonessential amino acids (GIBCO), 1% sodium pyruvate (GIBCO), 0.25% $NaHCO_3$ (MERCK), 1% vitamins (GIBCO), 1% Penicillin-Streptomycin (GIBCO), 0.2% Gentamycin (SIGMA), $3.5 \times 10^{-4}$% 2-Mercaptoethanol (SIGMA), 0.2% Bovine serum albumin (SIGMA), 1.8 mM $CaCl_2$, 50 mM KCl, 0.8mM $MgSO_4$, 0.1 M NaCl, 10 mM Glucose, 50 µM Phenol Red). Subsequently the cells were incubated for 12 hours in phosphate-free medium supplemented with 1 mCi 32P $PO_4$ (AMERSI tAM) at 37° C. and 100% humidity in sterile flasks (GREINER). After 12 hours, the cells were harvested from the flasks, and washed twice in PBS (SEROMED). The cells were then lysed in 1.6 ml lysis buffer (20 mM TRIS-HCl, pH 7.5 (MERCK), 150 mM NaCl (MERCK), 10 mM NaF, 1 mM EDTA (MERCK), 10 µg/ml Aprotinin (SIGMA), 50 µ g/ml Leupeptin (SIGMA), 1 mM PMSF (SIGMA). 1 mM Na-Vanadate (MERCK)) for 45 minutes at 4° C. As detergent, 1% TRITON X-100 (PERCE) or 1% digitonin (SIGMA) was added to the lysis buffer. After solubilization, the nuclei were spun out at 4° C. in an Eppendorf centrifuge at 13,000 RPMs for 15 minutes. The postnuclear lysates were then preabsorbed 2 times with 25 µl of an irrelevant monoclonal antibody (IgG1, 6 mg/ml) coupled to CNBr activated protein A sepharose for 30 minutes. The sepharose beads were spun down and replaced with fresh beads. The lysates were then incubated for 1 hour at 4° C. with an anti-CD45 monoclonal antibody (Gap 8.3 from hybridoma HB12, ATCC) bound to CNBr activated sepharose beads. The sepharose beads were subsequently spun down again, and washed 3 times with lysis buffer. They were then resuspended in 60 µl SDS sample buffer (10 % Glycerol (ROTI t), 3% SDS (SERVA), 0.625 M TRIS-tHCl, pH 6.8, 0.001% Bromphenol blue (SERVA)) and boiled for 5 minutes in order to dissociate the antigen-antibody complex. The analysis of the immunoprccipitated proteins was performed by means of SDS gel electrophoresis as shown in FIG. 1 and described in the related description.

Example 2. Determination of tile Isoelectric Point of pp32

Immunoprecipitates from human T lymphocytes labeled in vivo with $32PO_4$ were obtained as described in Example 1. The CD45 immunoprecipitates were boiled in SDS sample buffer and subsequently separated from the sepharose beads in a biotrap electroelution chamber (SCHLEICHER & SCHUELL) in SDS running buffer (0.025 M TRIS HCl, pH 8.0 0.192 M Glycin (MERCK), 0.1% SDS) at 100 V overnight. This was followed by a buffer exchange to 15 mM ammonium bicarbonate (ROTH). Subsequently the diluted proteins were precipitated by adding double the volume of acetone and freezing the samples for 30 minutes at 20 ° C. using 10 µg of bovine serum albumin added previously as a carrier protein. The precipitates were spun down (15 minutes, 10,000 RMPI, Eppendorf Centrifuge, 4° C.) and the acetone was aspirated. Remaining acetone was evaporated by placing the sample in a Lyophylizer for 5 minutes. Finally the precipitate was washed with 60 µl $ddH_2O$ and dried again for one hour.

Figure 2:
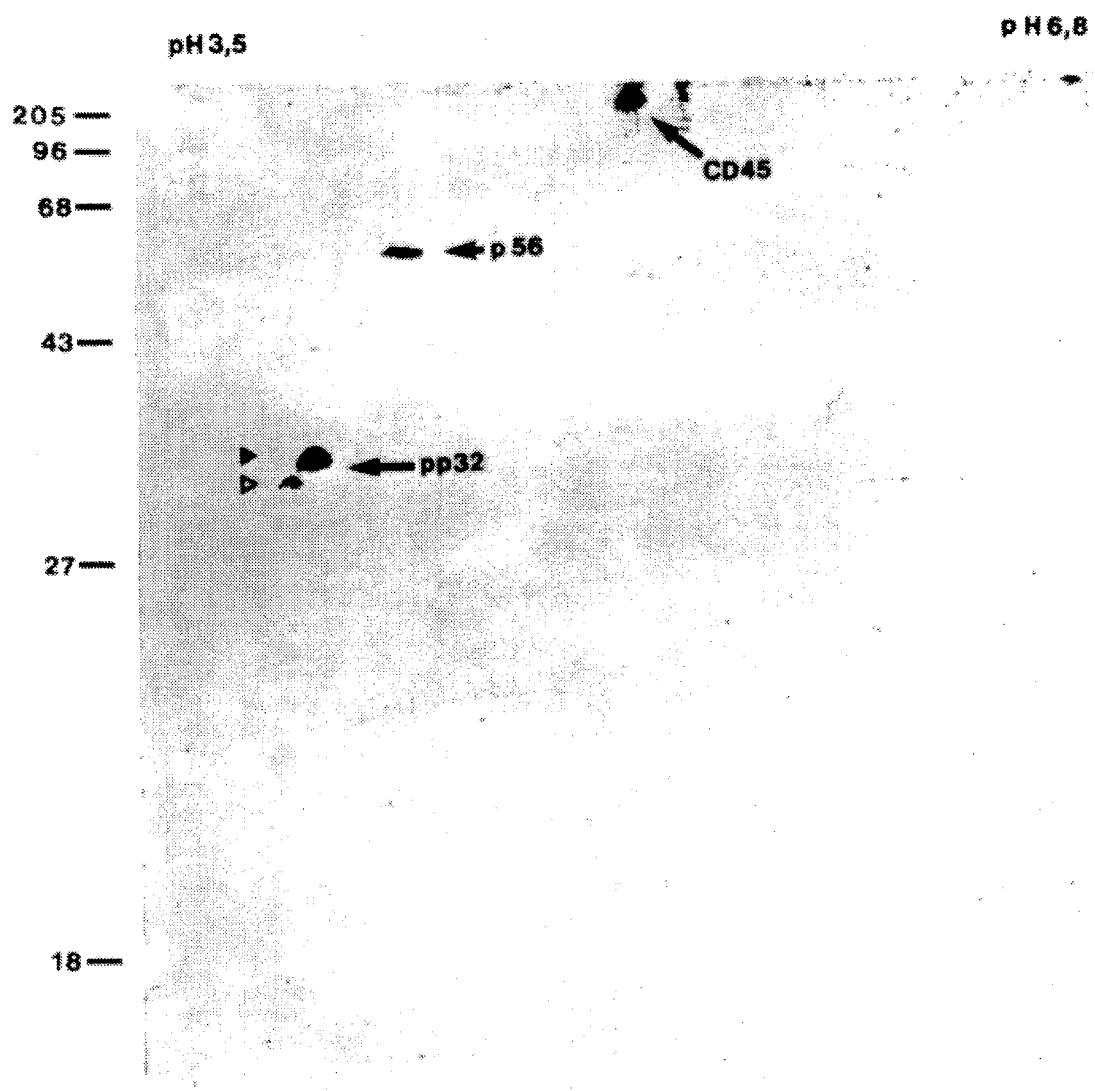
FIG. 2: Determination of the isoelectric point of pp32 by two dimensional gel electrophoresis

In order to determine the isoelectric point of the immunoprecipitated proteins, two dimensional gel electrophoresis was performed according to the protocol of O'Farrel. The electroluted and dried proteins were resuspended in 40 g µl of O'Farrel buffer for two dimensional gel electrophoresis (18 % NP-40 (SERVA) 3.6 % Ampholine pH 3.5–10, 14.4% Ampholine pH 6.0–8.0 (LKB), 0.45 M Dithiothreitol (DTT, SIGMA)) and loaded on a 1 mm tube gel (pH gradient from 3.5 to 7.5 according to O'Farrel, prerun 15 minutes, 200 V, 30 min, 300 V, 30 min, 400V)). The sample was overlaid with 10 µl 6 M urea. The tube as well as the upper electrophoresis chamber were filled with 100 mM NaOH. The buffer for the lower chamber was a 0.085 % $H_3PO_4$ solution. The isoelectric focusing procedure was performed for 16.5 hours at 400 V and 1.5 hours at 800 V (total of 7,800 V-hours). Subsequently the two tubes were equilibrated in 0.12 M TRIS-HCl, pH 6.8, 2% SDS, 0.05 M DTT, 10% Glycerol, 0.02% Bromphenol blue according to the protocol of Lefkowitz and loaded on an 18% acrylamide gel in order to separate the proteins in the second dimension by molecular weight. The localization of the separated proteins was determined by autoradiography. See FIG. 2 and related description.

Example 3. In vitro Phosphorylation of pp32

The method used to phosphorylate proteins in vitro is similar to that described in Example 1, the difference being that the anti-CD45 immunoprecipitates are obtained from T lymphocytes not previously incubated with radioactive orthophosphate. After the immunoprecipitation of the CD45 molecule and the subsequent washing steps, sepharose beads were resuspended in 40 µl kinase buffer (20 mM TRIS-HCl, pH 7.5, 0.1% digitonin, 10 mM $MnCl_2$ (MERCK)), to which 10 µCi 32P-ATP (AMERSHAM) had been added and incubated for 20 minutes at room temperature. During the kinase reaction, which requires Mn as an essential cofactor, the radioactive ATP is being cleaved by the kinase into ADP and the terminal phosphate group transferred to the substrate. The substrate can be either an associated molecule in the immunoprecipitate or the protein kinase itself. After 20 minutes the enzymatic reaction is stopped by adding 1 ml stopping buffer (20 mM TRIS-HCl, pH 7.5, 150 mM NaCl, 20 mM EDTA, 0.1% digitonin). The sepharose beads are subsequently washed twice with 1 ml of stop buffer resuspended in 60 µl SDS sample buffer, boiled, and electrophoretically analyzed.

Figure 3A:
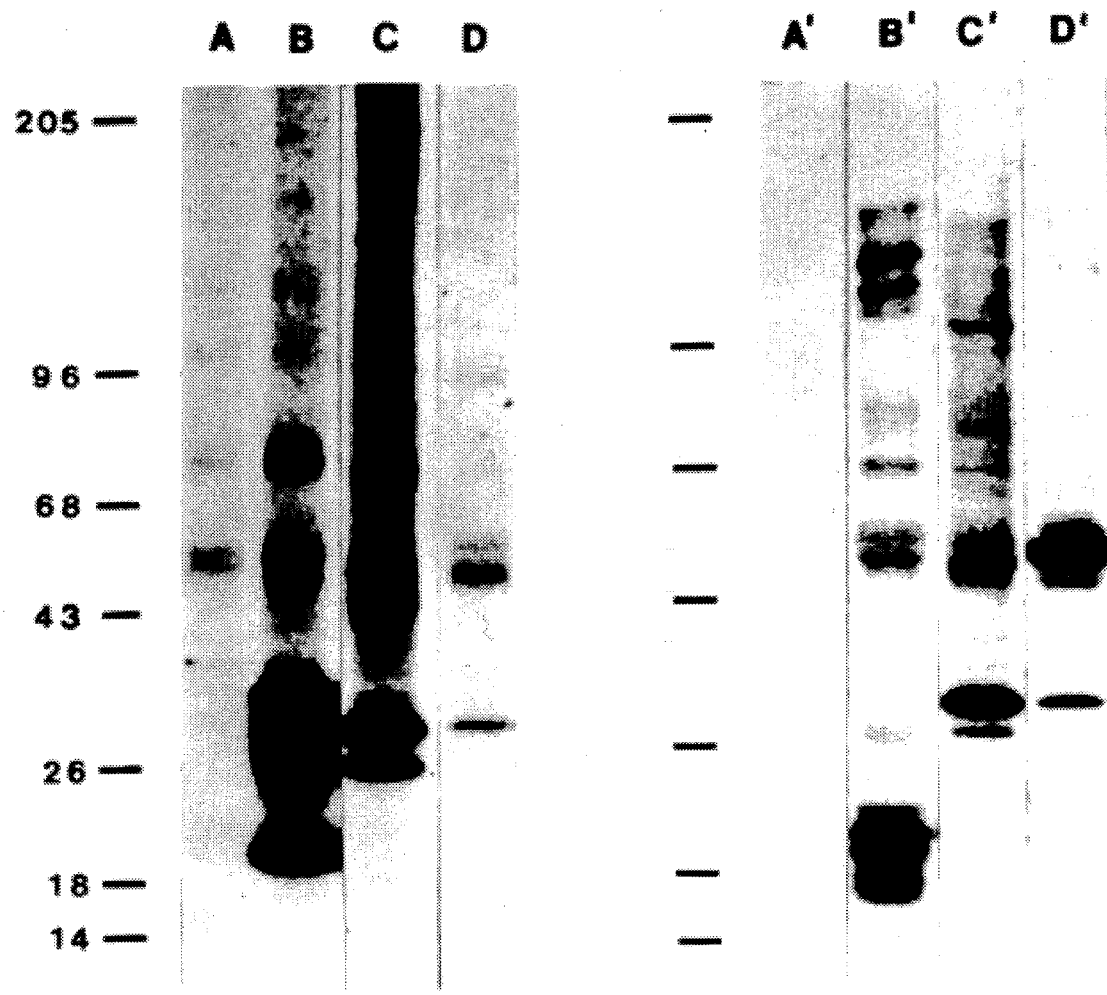
FIG. 3A: In vitro phosphorylation of pp32 Lane A: sepharose alone; Lane B: sepharose coupled with an anti-CD3 mAb (OKT3; Ortho); Lane C: sepharose coupled with an anti-CD45 mAb (Gap 8.3 from hybridoma ATCC HB 12); Lane D: sepharose coupled with anti-CD4 mAb (OKT4, Ortho).
Figure 3B:
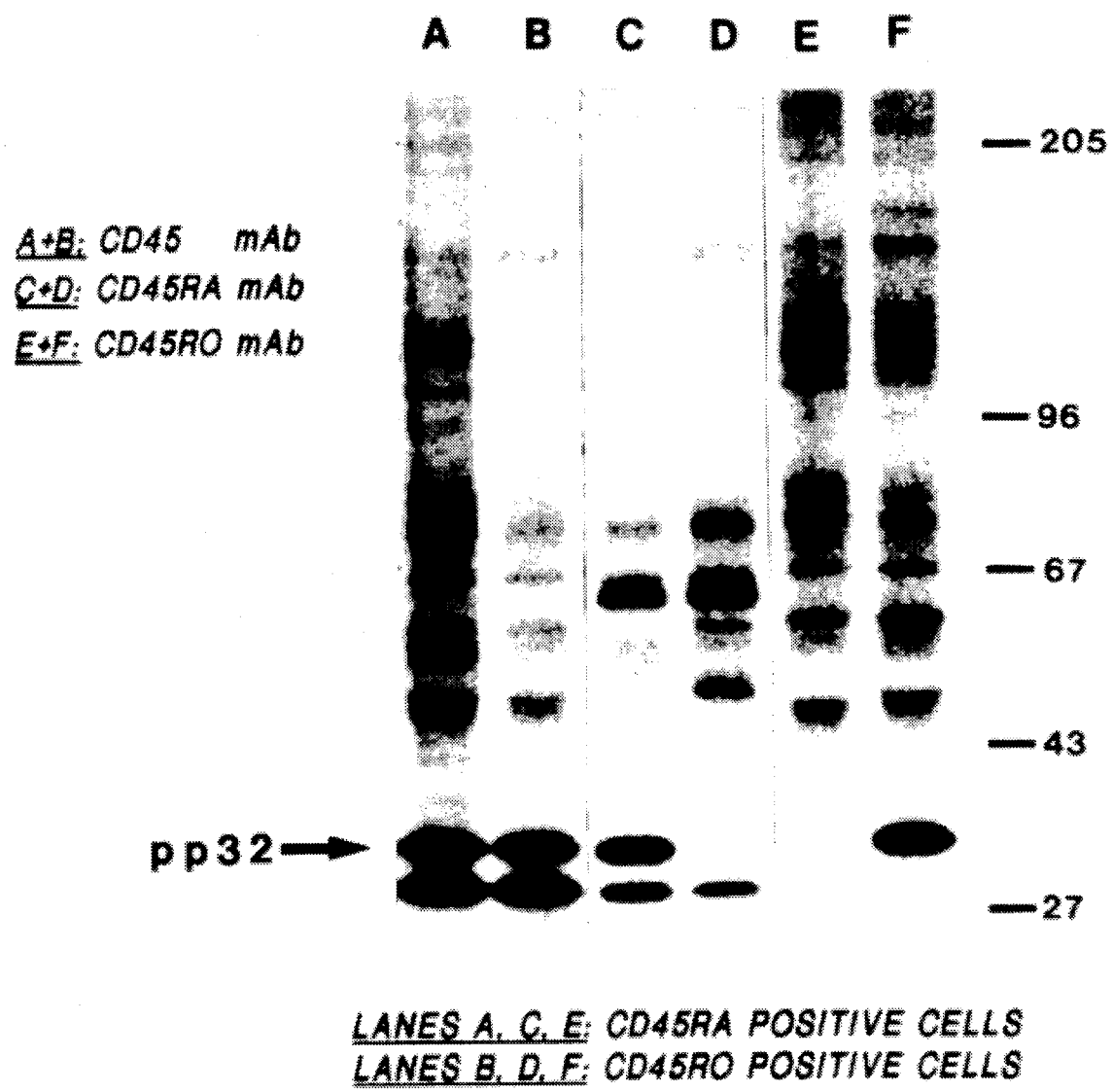
FIG. 3B: Lanes A and B: anti-CD45 mAb (Gap 8.3); Lanes C and D: sepharose coupled with CD45RA mAb 2H4 (Coulter) that reacts with the 220kD isoform of CD45; Lanes E and F: sepharose coupled with UCHL-1 mAb (DAKO) that reacts with the 180 kD isoform of CD45. Lanes A, C, E: immunoprecipitates from T cells that do not express the 180 kD isoform of CD45. Lanes B, D, F: immunoprecipitates from T cells that do not express the 220 kD isoform of CD45.

FIG. 3A shows that pp32 is only phosphorylated in vitro if an anti-CD45 monoclonal antibody had been used for the immunoprecipitation. Both the isotype of the mAb and the epitope recognized by the anti-CD45 antibody are irrelevant. On the other hand, pp32 is phosphorylated in vitro only if the anti-CD45 monoclonal reacts with a CD45 molecule (FIG. 3B). This rules out non-specific binding and phosphorylation of pp32. A monoclonal antibody directed against CD3 shows a totally different protein pattern (FIG. 3A). Therefore, coprecipitation and the in vitro phosphorylation of pp32 is dependent upon immunoprecipitation of CD45 by anti-CD45 antibodies. A monoclonal antibody directed against CD4 shows a weak phosphorylation of pp32 (FIG. 3A). This phenomenon suggest that CD45 and CD4 are associated with the same set of molecules.

Example 4. Existence of pp32 in Different Cells

Figure 4:
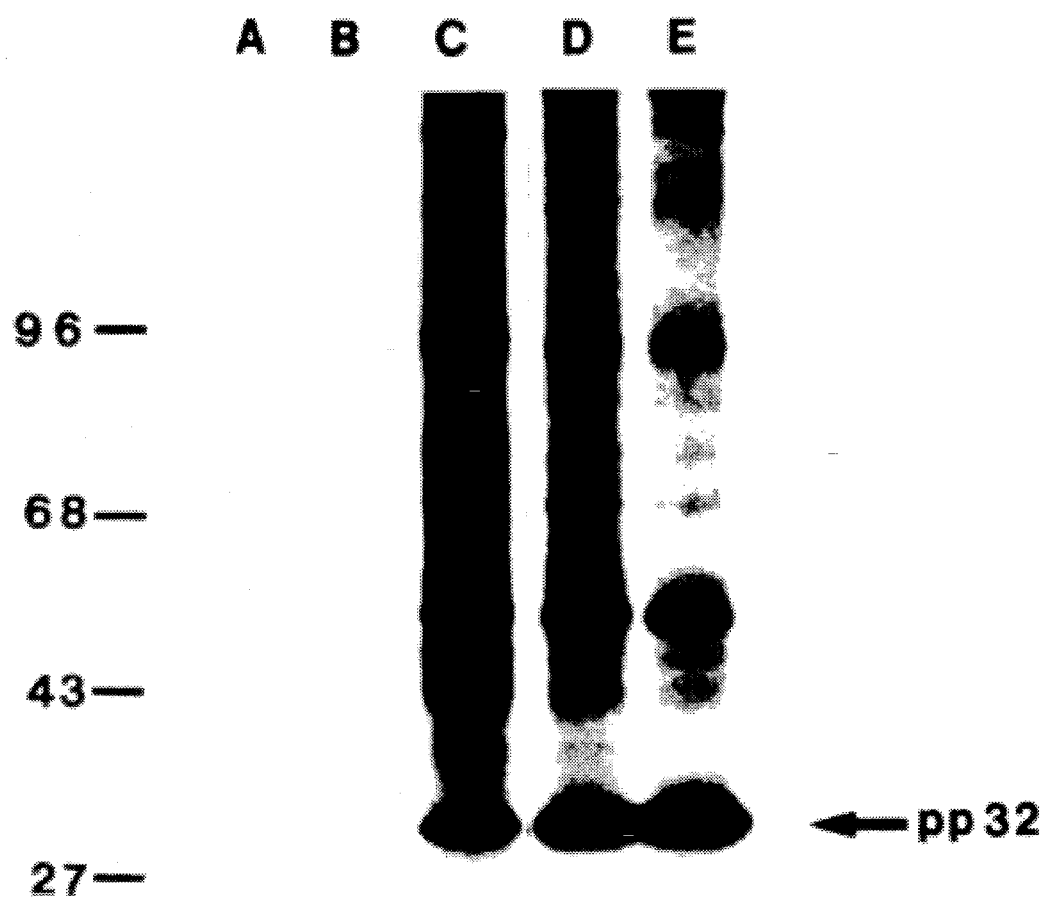
FIG. 4:CD45 immunoprecipitation from different cell lines
Figure 5:
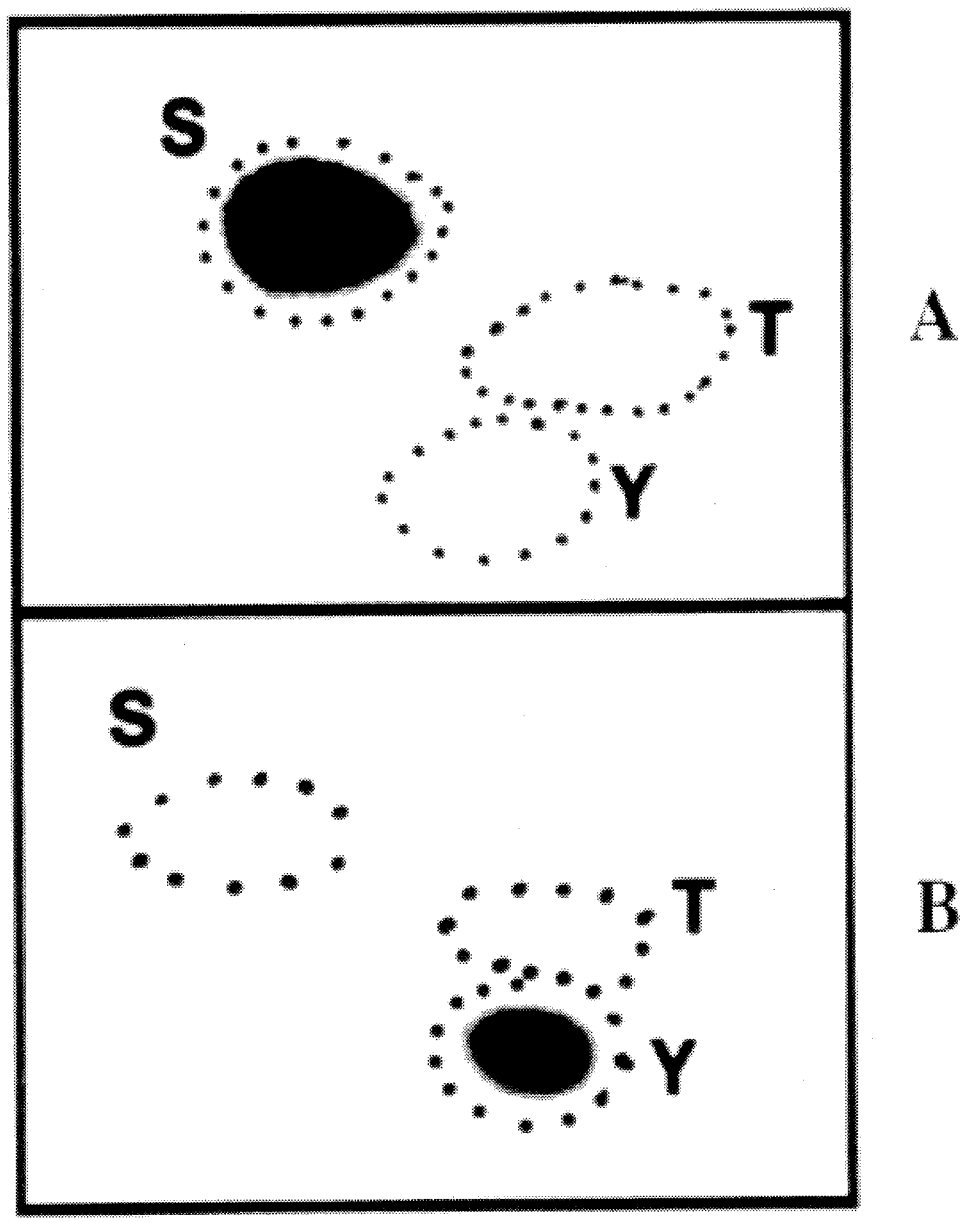
FIG. 5: Phosphoaminoacid analysis of in vivo and in vitro phosphorylated pp32. A: in vivo phosphorylated pp32 from resting T cells; B: in vitro phosphorylated pp32.

CD45 immunoprecipitates were performed with the following cell lines: EBV-Transformed B-cell in our case CD45RFi line Laz-509 (CD45RA positive), T-cell line Jurkat (CD45RA), T-cell line HPB-ALL (CD45 negative), erythroid tumor cell line K562 (CD45 negative). $1\times10^7$ cells were lysed in digitonin lysis buffer and CD45 immunoprecipitates were preformed as described in example 1. The samples were subsequently in vitro kinased. The analysis of the phosphorylated proteins was done by means of SDS gel electrophoresis and autoradiography. See FIG. 4 and related description.

Example 5. Phosphoamino Acid Analysis

CD45 immunoprecipitates that had been obtained from digitonin lysed T lymphocytes were separated by means of electrophoresis and the location of pp32 was determined by autoradiography. 32p labeled pp32 was then cut out of the gel and rehydrated for 30 minutes in SDS sample buffer. The pp32 protein was subsequently electroeluted out of the rehydrated pieces of the gel as described in example 2. After acetone precipitation the protein was washed in 60 µl $H_2O$ and dried for one hour in a lyophilizer. Then 100 µl of 5.7 M HCl were added to the protein pellet. The tube was subsequently incubated for an additional hour at 110° C. to allow acid hydrolysis of phosphoamino acids, and the precipitate dried overnight in a lyophilyzer. The phosphoamino acid analysis was performed by means of two dimensional thin layer chromatography on cellulose mats (MERCK). The separation of the first dimension was done for 45 minutes at 1500 V at pH 1.9 (88% formic acid: acetic acid: $H_2O$ = 50: 156: 1794) and in the second dimension for 30 minutes at pH 3.5(Pyridin: acetic acid: $H_2O$ =10:100:1890). The location of amino acid standards was determined by nonhydrin staining. The location of the 32p labeled amino acids was determined by autoradiography.

In vivo labeled pp32 obtained from resting T cells is phosphorylated on serine residues. In contrast, pp32 labeled by in vitro kinasing is exclusively phosphorylated on tyrosine. This suggests the presence of a tyrosine kinase in the CD45 immunoprecipitate.

Example 6. Identification of the Tyrosine Kinase

Immunoprecipitates from resting T cells were obtained by adding either anti-CD45 or anti-CD4 (OKT4, Ortho) mAbs to T cells solubilized in the detergent Brij 58 (1% v/v, Pierce). The anti-CD4 monoclonal antibody was used because the CD4 molecule has been shown to be associated with the tyrosine kinase $p56^{lck}$. Subsequently, the immunoprecipitates were kinased in vitro as previously described. The analysis of the coprecipitated proteins was done by means of autoradiography of the dried SDS gel. The bands that represent p56 lck were cut out of the dried gel and rehydrated for 15 minutes in 100 µl SDS sample buffer to which V8 protease (SIGMA) had been added at a concentration of 100 µg/ml. The rehydrated gel slices were loaded on a second SDS gel (15–22.5%, 1.5 mm thickness) and incubated for another 30 minutes. The electrophoresis was run at 50 V until the sample butler had completely penetrated the stacking gel. Subsequently, the voltage was increased for four hours to 70 V and then the power was switched off for 30 minutes. The electrophoresis was then performed under standard conditions. After drying the gel, the location of the peptides was determined by means of autoradiography.

Figure 6:
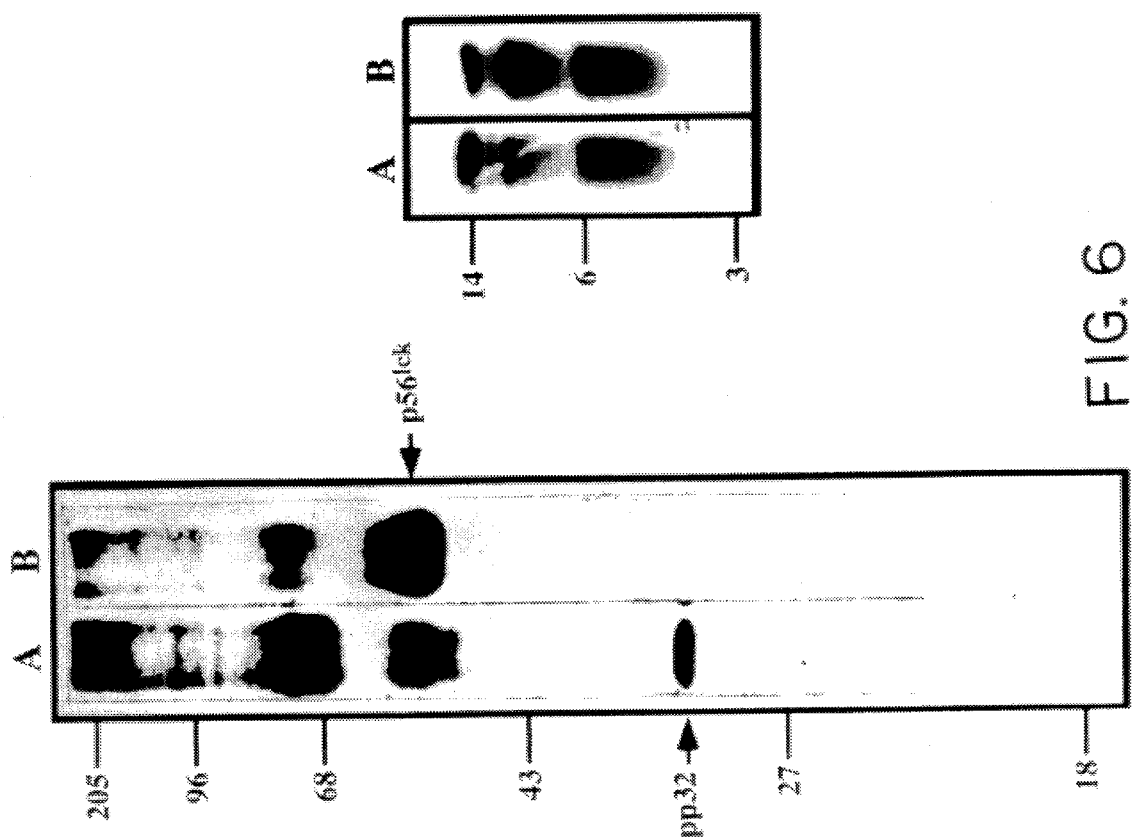
FIG. 6: Characterization of the CD45 associated tyrosine kinase A: in vitro phosphorylation pattern of CD4 and CD45 immunoprecipitates obtained from T cells lysed with 1% Brij 58 (Lane A: CD45 immunoprecipitate; Lane B: CD4 immunoprecipitate. B: V8 protease digest of the 56kD doublet band from A: Lane A and B as above.

See FIG. 6 and related description. Example A is an anti-CD45 immunoprecipitate. Besides pp32, there is an in vitro labeled doublet of apparent molecular weight 56kD. The doublet has the same electrophoretic mobility as $p56^{lck}$ coprecipitated with the anti-CD4 mAb. These data suggest that the proteins are identical. Further proof of their homology is given by the V8 protease digestion in Example B. The peptide patterns of both doublets are identical. Therefore, the protein kinase that phosphorylated pp32 in vitro is assumed to be $p56^{lck}$.

Example 7. Dephosphorylation of pp32 by Purified CD45

Figure 7:
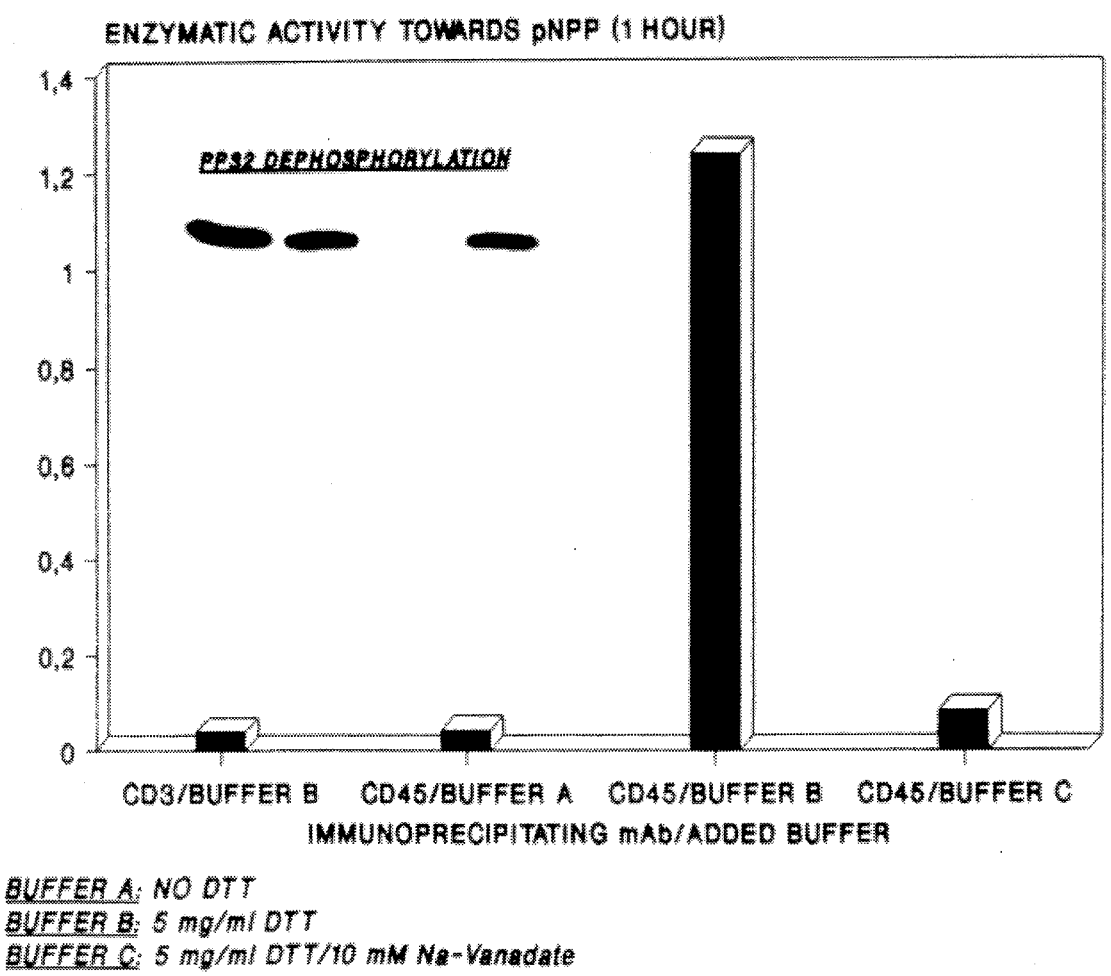
FIG. 7: In vitro dephosphorylation of pp32 by CD45 Lane A: in vitro phosphorylated pp32 incubated with purified CD3 in the presence of DTT; Lane B: In vitro phosphorylated pp32 incubated with inactive CD45; Lane C: in vitro phosphorylated pp32 incubated with CD45 that had been activated with DTT; Lane D: in vitro phosphorylated pp32 incubated with DTT-activated CD45 in the presence of sodium-orthovanadate (10 mM, Merck).

As previously described, pp32 is only phosphorylated in vitro if the CD45 immunoprecipitate has been obtained from digitonin lysed cells. This argues for a weak interaction between $pp32/56^{lck}$ and CD45. In order to demonstrate the dephosphorylation of pp32 by CD45, T cells were lysed in digitonin. The immunoprecipitates from digitonin lysed cells were phosphorylated in vitro. After having stopped the reaction by addition of EDTA the immunoprecipitates were washed and subsequently incubated for 10 minutes at 4° C. in 40 µl of stop buffer to which 1% Triton X-100 had been added. This treatment leads to a disruption of the CD45/ pp32 complex and to the release of unbound pp32. The released pp32 was then added to the CD45 immunoprecipitates that had been obtained from Triton X-100 lysed T cells. Dithiothreitol (DTT, Sigma), was added to the buffer at a final concentration of 3 µg/ml in order to activate the CD45 molecule in vitro. In a control sample sodium orthovanadate (10 mM Merck), was added to inhibit the phosphatase activity of the CD45 molecule. See FIG. 7 and related description.

If CD45 is not activated by DTT, no dephosphorylation of pp32 can be observed. If CD45 is activated by the addition of DTT, pp32 shows complete dephosphorylation. Inhibition of activated CD45 by vanadate prevents the dephosphorylation of pp32. A control CD3 immunoprecipitate did not show any phosphatase activity in the presence of DTT. Therefore, the in vitro dephosphorylation of pp32 is dependent upon the phosphatase activity of CD45. This suggests that pp32 might be a substrate for CD45 in vivo.

Example 8. Modifications to pp32Associated with T Cell Activation $1\times10^7$ Jurkat cells ($10^7$cells/ml RMPI 1640, 10% FCS) were activated for various times with PMA (final concentration $10^{-8}$ M). As a control, unstimulated Jurkat were used. The cells were washed once with ice cold PBS and then lysed in 1 ml of digitonin lysis buffer. The soluble fraction was immunoprecipitated with anti-CD45 mAb. The immunoprecipitates were washed and subsequently kinased in vitro. After washing in stop buffer the samples were boiled in sample buffer. The immunoprecipitates were run out on an 18% acrylamide gel in order to obtain better resolution of the 32 kD range.

Figure 8:
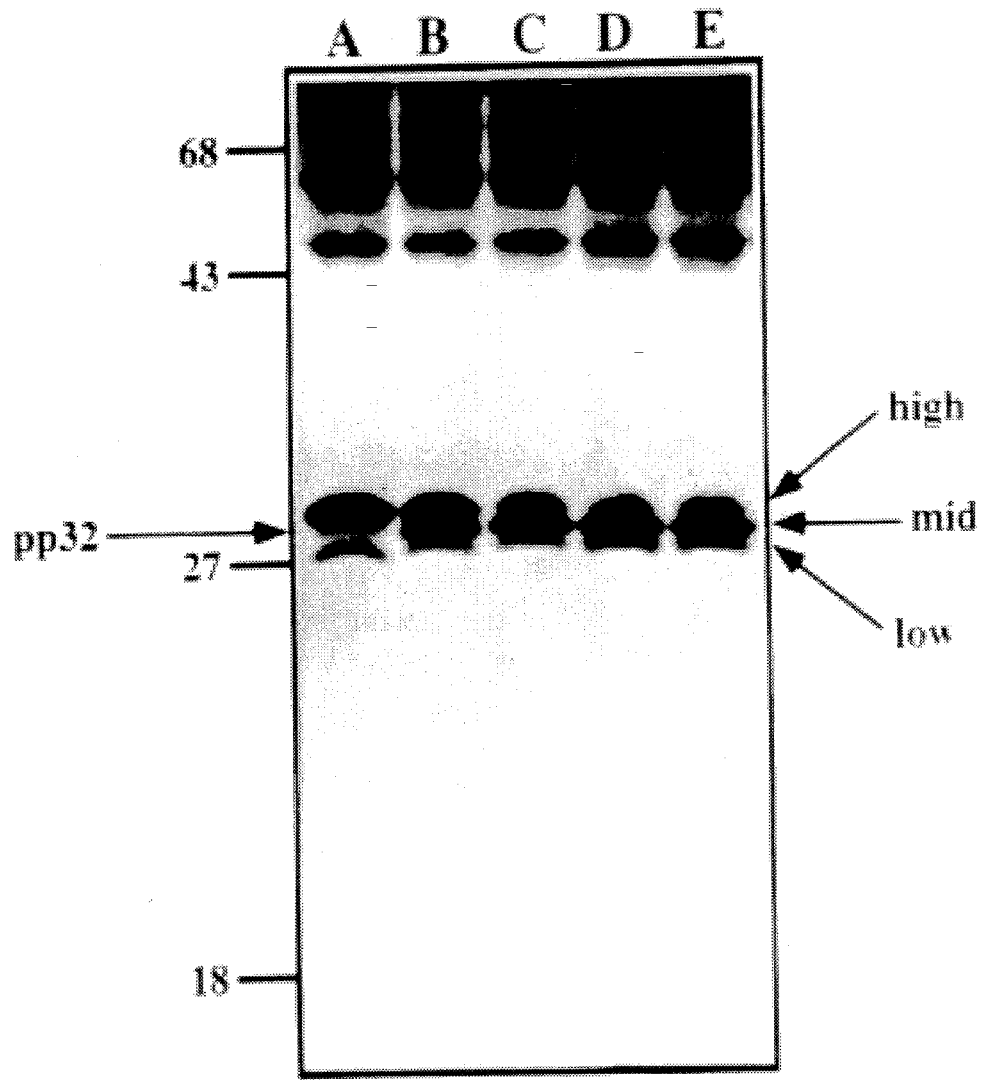
FIG. 8: Changes in in vitro labeled pp32 in the course of T cell activation Lane A: pp32, unstimulated T lymphocytes; Lane B: pp32; T cells stimulated for 5 minutes with PMA; Lane C: pp32; T cells stimulated for 10 minutes with PMA; Lane D: T cells stimulated for 30 minutes with PMA; Lane E: T cells stimulated for one hour with PMA.

See FIG. 8 and related description. On an 18% SDS gel, in vitro labeled pp32 obtained from unstimulated Jurkat can be seen as two distinct bands, approximately 2kD apart from each other. Upon stimulation of the T lymphocytes with PMA, the intensity of the upper band decreases in the samples kinased in vitro after 5 minutes of stimulation. However, a third band located between the upper and lower ones, starts to appear. This process is time dependent and complete after about 30 minutes. The lower band seems not to undergo any changes in the in vitro phosphorylation assay.

Example 9. Isolation of a cDNA Encoding pp32

In order to isolate a cDNA encoding pp32, the amino acid sequences of several peptide fragments (from the amino terminal and from tryptic and V8 protease digestion) of pp32 were determined. These amino acid sequences are as follows:

| N terminus (N): | |
|---|---|
| SGGSAEDSVG | (SEQ ID NO:3) |
| Tryptic Fragments (T1–T4) | |
| T1 GGYYHPAR | (SEQ ID NO:4) |
| T2 LLWASPP | (SEQ ID NO:5) |
| T3 WLQAR | (SEQ ID NO:6) |
| T4 AAGGQGLHVTAL | (SEQ ID NO:7) |
| V8 Fragments (V1–V4) | |
| V1 LGSTDNDLERQ | (SEQ ID NO:8) |
| V2 EDEQDTDYDHV | (SEQ ID NO:9) |
| V3 GDLVLGSPGPASAGGSAE | (SEQ ID NO:10) |
| V4 ALLSDLHAFAGSAAWDDSARA | (SEQ ID NO:11) |

The sequences of the peptide fragments were used to design sets of degenerate oligonucleotides representing the ambiguous DNA sequence encoding portions of the polypeptides. The nucleotide sequences of these primers are shown below:

| Stage 1: | | |
|---|---|---|
| 21AF1 | YTN TCN GAY CTN CAY GC | (SEQ ID NO:12) |
| 21AF2 | YTN TCN GAY TTR CAY GC | (SEQ ID NO:13) |
| 21AF3 | YTN AGY GAY CTN CAY GC | (SEQ ID NO:14) |
| 21AF4 | YTN AGY GAY TTR CAY GC | (SEQ ID NO:15) |
| 21AR1 | GC NCK NG3C NGA RTC RTC | (SEQ ID NO:16) |
| 21AR2 | GC NCK NGC RCT RTC RTC | (SEQ ID NO:17) |
| Stage 2: | | |
| 11V8F | GAR CAR GAY ACN GAY TA | (SEQ ID NO:18) |
| 21V8R | TCC CAG GCA GCA GAG CCA GCA | (SEQ ID NO:19) |

(Y = C and T; R = A and G; K = G and T; N = A, C, G and T).

The oligonucleotides were used in various combinations as primers in the polymerase chain reaction (PCR) to sucessfully amplify short cDNA fragments encoding pp32. One cDNA fragment so isolated was used as a probe to screen a cDNA library to obtain full-length cDNA clones.

Amplification of 56 bp cDNA encoding 19 amino acids of peptide V4

PolyA+ RNA was prepared from the human cell line Jurkat and was reverse transcribed into double-stranded cDNA using the RNAseH- reverse transcriptase kit and protocol supplied by Gibco. Approximately 20 ng of this cDNA was used as the template in 8 PCR reactions with primers as follows: Four degenerate sense primers (designated 21AF1-21AF4; shown above) corresponding to amino acids LSDLHA in peptide V4 (amino acid positions 3 to 8, inclusive, of SEQ ID NO: 11 ) were each paired with two degenerate antisense primers (designated 21AR1 and 21 AR3; shown above) corresponding to the sequence DDSARA in peptide V4 (amino acid positions 16 to 21, inclusive, or SEQ ID NO: 11 ). The degenerate primers were used at a concentration of 2 to 10 pmol per permutation per 100 ul reaction. Cycling parameters were as follows: after an initial 4 minute incubation at 94° C., samples were taken to 94° C. for 1 minute, ramped over 2.5 minutes to an annealing temperature of 37° C. for 2 min. and then ramped over a 2.5 minute interval to 72° C. for 2 minutes. This was repeated for two more cycles followed by an additional 30-37 cycles as above except that a 55° C. annealing temperature and minimal ramp times were chosen. In order to generate sufficient quantities of PCR products for visualization by ethidium bromide staining, each of the 8 reactions was reamplified using as template 0.1 ul of the primary reaction. These secondary reactions were carried out for 25 cycles (30".94° C./1',55° C./1',72° C.). Two of the 8 PCR reactions produced bands in the corr range. In order to clone the PCR fragments of interest, a third amplification reaction was performed using as template 0.1 ul of the 2 secondary reactions containing the product of interest. The primers used for the tertiary amplification were identical to the secondary primers except that they were extended at the 5' end by the nucleotide sequence: 5' GAG TAG TCG AC 3' (SEQ ID NO: 20), which generates a Sal I restriction site suitable for cloning. The PCR products of interest were thus cloned and sequenced. One clone contained 22 base pairs between the primer-derived sequences which encoded the sequence FAGSAAW present in the V4 peptide (amino acid positions 9 to 15, inclusive, in SEQ ID NO: 11 ).

Cloning of a 242 base pair cDNA fragment of pp32 by PCR

The actual DNA sequence encoding the FAGSAAW peptide (determined above) was used to design a non-degenerate antisense oligonucleotide primer (see FIG. 1 ) used in conjunction with a degenerate sense primer based on the EQDTDY peptide sequence within peptide V2 (amino acid positions 3 to 8, inclusive, in SEQ ID NO: 9). The PCR conditions were as above. This produced a 242 base pair cDNA fragment representing the partial sequence of pp32 and encoding peptide V3. This cDNA is designated probe A.

Cloning of full-length pp32 cDNA

Probe A was radioactively labeled according to standard methods and used to screen a Jurkat cell cDNA library purchased from Stratagene in a solution consisting of 3.5X SSC, 1X Denhardt's solution, 0.4% SDS, 50 ug/ml salmon sperm DNA and 10% dextran sulfate at 65° C. The filters were washed in 2X SSC/0.1% SDS at 55° C. Approximately 30 positive clones were obtained out of 700,000 plaques screened. The longest clones were selected for farther sequencing and analysis. The nucleotide sequence of clone 8 is shown in SEQ ID NO: 1 and the predicted amino acid sequence of the encoded protein is shown in SEQ ID NO: 2. The identity of this cDNA clone as pp32 was further confirmed by an experiment demonstrating that the clone directed the synthesis of a polypeptide in vitro, which migrated in polyacrylamide gels at 32 kD, and was immunoreactive with an anti-serum raised against Jurkat cell-derived pp32 protein.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated pp32 protein which can associate with CD45 comprising an amino acid sequence shown in SEQ ID NO: 2.

2. The isolated pp32 protein of claim 1 which is human.

3. The isolated pp32 protein of claim 1 which is phosphorylated.

4. The isolated pp32 protein of claim 1 which is not phosphorylated.

* * * * *

UNITED STATES PATENT AND TRADEMARK OFFICE
CERTIFICATE OF CORRECTION

PATENT NO. : 5,510,461
DATED     : April 23, 1996
INVENTOR(S) : Stefan Meuer et al It is certified that error appears in the above-identified patent and that said Letters Patent is hereby corrected as shown below:

On the title page: Item [54] and Column 1, line 1, change "PP" to --pp32--
Column 2, line 31, change "or" to --of--
Column 3, line 55, change "ttPB-ALL" to --HPB-ALL--
Column 3, line 59, change "HPBALL" to --HPB-ALL--
Column 4, line 34, change "HB 12" to --HB12--
Column 9, line 8, change "bund" to --found--
Column 11, line 25, change "etal." to --et al.--
Column 13, line 40, change "sulfite" to --sulfate--
Column 14, line 8, change "filters" to --titers--
Column 14, line 28, change "Iluse" to --Huse--

UNITED STATES PATENT AND TRADEMARK OFFICE
CERTIFICATE OF CORRECTION

PATENT NO. : 5,510,461
DATED : April 23, 1996
INVENTOR(S) : Stefan Meuer et al.

It is certified that error appears in the above-identified patent and that said Letters Patent is hereby corrected as shown below:

Column 17, line 53, change "TRIS-tHCI" to --TRIS-HCl--
Column 17, line 56, change "immunoprccipitated" to --immunoprecipitated--
Column 18, line 7, change "20 °C" to -- -20° C--
Column 19, line 44, change "nonhydrin" to --ninhydrin--
Column 20, line 3, change "butler" to --buffer--
Column 21, line 48, change "NG3C" to --NGC--
Column 22, line 26, change "corr" to --correct size--
Column 22, line 32, change "GAG" to --GAC--
Column 22, line 61, change "father" to --further--

Signed and Sealed this

Ninth Day of December, 1997

BRUCE LEHMAN

Attest:

Attesting Officer    Commissioner of Patents and Trademarks